United States Patent [19]

McCormick et al.

[11] Patent Number: 5,691,362
[45] Date of Patent: Nov. 25, 1997

[54] SUBSTITUTED BENZENE-FUSED HETERO- AND CARBOCYCLICS AS NUEROKININ ANTAGONISTS

[75] Inventors: Kevin D. McCormick, Edison; Andrew T. Lupo, Jr., Emerson, both of N.J.

[73] Assignee: Schering-Plough Corporation, Kenilworth, N.J.

[21] Appl. No.: 658,790

[22] Filed: Jun. 5, 1996

Related U.S. Application Data

[63] Continuation-in-part of Ser. No. 469,315, Jun. 6, 1996, abandoned.

[51] Int. Cl.$^6$ .................. A61K 31/40; C07D 209/16; C07D 209/20; C07D 333/58
[52] U.S. Cl. .................. 514/339; 514/414; 514/415; 514/443; 546/277.4; 548/454; 548/467; 548/503; 549/503
[58] Field of Search .................. 548/454, 467, 548/503; 546/277.4; 549/49; 514/339, 414, 415, 443

[56] References Cited

U.S. PATENT DOCUMENTS 5,350,852  9/1994  Emonds-Alt et al. .................. 544/336

FOREIGN PATENT DOCUMENTS

| 591 040 | 4/1994 | European Pat. Off. . |
|---|---|---|
| 699674 | 3/1996 | European Pat. Off. . |
| 2274777 | 8/1994 | United Kingdom . |
| WO 93/18023 | 9/1993 | WIPO . |
| WO 94/29309 | 12/1994 | WIPO . |

OTHER PUBLICATIONS

Maggi et al, *Eur. J. Pharmacol.*, 166, (1989), pp. 435–440.
Ellis et al, *J. Pharmacol. Exp. Ther.*, 267, 1 (1993), pp. 95–101.
Furchgott, *Pharm. Rev.*, 7 (1955), pp. 183–265.
Arunlakshana et al, *Brit. J. Pharmacol.*, 14, 48 (1959), pp. 48–58.
Danko et al, *Pharmacol. Comm.*, 1, 3 (1992), pp. 203–209.
Chung et al, *Molecular Pharmacology*, 48 (1995), pp. 711–716.
Omura et al, *Tetrahedron*, 34 (1978), pp. 1651–1660.
Burkholder et al, *Bioorganic Med. Chem. Let.*, 6, 8 (1996), pp. 951–956.

*Primary Examiner*—Fiona T. Powers
*Attorney, Agent, or Firm*—Anita W. Magatti

[57] ABSTRACT

Compounds represented by the structural formula

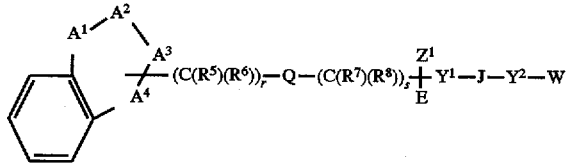

or a pharmaceutically acceptable salt thereof, wherein the variables are as defined in the specification; methods of treating asthma, cough, bronchospasm, inflammatory diseases, and gastrointestinal disorders with said compounds, and pharmaceutical compositions comprising said compounds are disclosed.

20 Claims, No Drawings

SUBSTITUTED BENZENE-FUSED HETERO- AND CARBOCYCLICS AS NUEROKININ ANTAGONISTS

CROSS REFERENCE TO RELATED APPLICATION

This is a continuation-in-part of U.S. Ser. No. 08/469,315, filed Jun. 6, 1996, now abandoned.

BACKGROUND OF THE INVENTION

The present invention relates to a genus of substituted benzene-fused hetero- and carbocyclics useful as antagonists of tachykinin receptors, in particular as antagonists of the neuropeptides neurokinin-1 receptor ($NK_1$) and/or neurokinin-2 receptor ($NK_2$) and/or neurokinin-3 receptor ($NK_3$).

Neurokinin receptors are found in the nervous system and the circulatory system and peripheral tissues of mammals, and therefore are involved in a variety of biological processes. Neurokinin receptor antagonists are consequently expected to be useful in the treatment or prevention of various mammalian disease states, for example asthma, cough, bronchospasm, inflammatory diseases such as arthritis, central nervous system conditions such as migraine and epilepsy, nociception, and various gastrointestinal disorders such as Crohn's disease.

In particular, $NK_1$ receptors have been reported to be involved in microvascular leakage and mucus secretion, and $NK_2$ receptors have been associated with smooth muscle contraction, making $NK_1$ and $NK_2$ receptor antagonists especially useful in the treatment and prevention of asthma.

Some $NK_1$ and $NK_2$ receptor antagonists have previously been disclosed: arylalkylamines were disclosed in U.S. Pat. No. 5,350,852, issued Sep. 27, 1994, and spiro-substituted azacycles were disclosed in WO 94/29309, published Dec. 22, 1994.

SUMMARY OF THE INVENTION

Compounds of the present invention are represented by the formula I

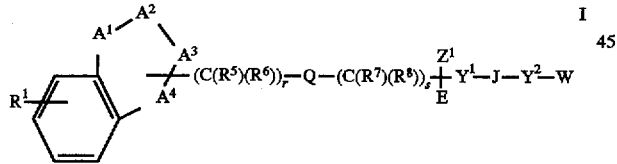

or a pharmaceutically acceptable salt thereof, wherein:

$A^1$, $A^2$, $A^3$ and $A^4$ are independently selected from the group consisting of $-(C(R^2)(R^{10}))-$, $-(C(R^{2c})(R^{10}))-$, $-(C(R^2))=$, $-(C(R^{2c}))=$, $-NR^{16}-$, $-N=$, $-O-$, $-S(O)_e-$, $-C(O)-$ and a bond, wherein $A^1$, $A^2$, $A^3$ and $A^4$, together with the carbon atoms to which they are attached, form a 5- or 6-membered ring, and wherein two adjacent A groups are selected from the group consisting of the following combinations:

$-(C(R^2)(R^{10}))-(C(R^2)(R^{10}))-$;
$-(C(R^2)(R^{10}))-(C(R^{2c}))=$;
$-(C(R^{2c})(R^{10}))-NR^{16}-$;
$-(C(R^{2c})(R^{10}))-N=$;
$-(C(R^{2c})(R^{10}))-O-$;
$-(C(R^{2c})(R^{10}))-S(O)_e-$;
$-(C(R^2)(R^{10}))-C(O)-$;
$-(C(R^2))=(C(R^2))-$;
$-(C(R^2))=N-$;
$=(C(R^2))-(C(R^2))=$;
$=(C(R^2))-NR^{16}-$;
$=(C(R^2))-N=$;
$=(C(R^2))-O-$;
$=(C(R^2))-S(O)_e-$;
$=(C(R^2))-C(O)-$;
$-NR^{16}-N=$;
$-NR^{16}-S(O)_e-$;
$-NR^{16}-C(O)-$;
$-N=N-$;
$=N-N=$;
$=N-O-$;
$=N-S(O)_e-$;
$=N-C(O)-$;
$-O-S(O)_e-$; and
$-O-C(O)-$;

provided that three adjacent A groups do not represent $-C(O)-O-C(O)-$, $-S(O)-O-C(O)-$ or $-S(O)-O-S(O)-$, and provided that when an aromatic nitrogen is present in the ring formed by $A^1$, $A^2$, $A^3$ and $A^4$, the N-oxide can be formed;

E is $R^3$-aryl or $R^3$-heteroaryl;

W is $R^4$-cycloalkyl, $R^4$-aryl, $R^4$-heterocycloalkyl or $R^4$-heteroaryl;

$R^1$, $R^3$ and $R^4$ are independently 1–3 substituents independently selected from the group consisting of H, halogeno, $C_1$–$C_6$ alkyl, $-CF_3$, $-C_2F_5$, $-OR^{11}$, $-COR^{11}$, $-CO_2R^{11}$, $-CON(R^{11})(R^{12})$, $-N(R^{11})(R^{12})$, $-N(R^{11})COR^{12}$, $-SH$, $-S(O)_eR^{13}$, $-OC(O)R^{11}$, $-OC(O)N(R^{11})(R^{12})$, $-NR^{11}CO_2R^{13}$, $-NR^{11}C(O)N(R^{12})(R^{14})$, $R^{15}$-phenyl, $R^{15}$-benzyl, $-NO_2$, $-NR^{11}S(O)_2R^{13}$ and $-S(O)_2NR^{11}R^{12}$; or adjacent $R^1$, $R^3$ or $R^4$ substituents can form a $-O-CH_2-O-$ group;

$R^2$ is independently selected from the group consisting of $R^{2a}$, $R^{2b}$ or $R^{10}$; and $R^{2c}$ is independently selected from the group consisting of $R^{2a}$ and $R^{10}$; wherein $R^{2a}$ is selected from the group consisting of $-CF_3$, $-C_2F_5$, $-COR^{11}$, $-CO_2R^{11}$, $-CON(R^{11})(R^{12})$, $R^{15}$-phenyl and $R^{15}$-benzyl; and $R^{2b}$ is selected from the group consisting of halogeno, $-OR^{11}$, $-NO_2$, $-N(R^{11})(R^{12})$, $-N(R^{11})COR^{12}$, $-SH$, $-S(O)_eR^{13}$, $-OC(O)R^{11}$, $-OC(O)N(R^{11})(R^{12})$, $-NR^{11}CO_2R^{13}$, $-NR^{11}C(O)N(R^{12})(R^{14})$, $-NR^{11}S(O)_2R^{13}$ and $-S(O)_2NR^{11}R^{12}$; provided that from any combination of ring members $A^1$, $A^2$, $A^3$ and $A^4$ comprising $R^2$ and $R^{2c}$, no more than one substituent can be selected from $R^{2a}$ and no more than one substituent can be selected from $R^{2b}$;

$R^5$, $R^7$, $R^9$, $R^{11}$, $R^{12}$ and $R^{14}$ are independently selected from the group consisting of H, $C_1$–$C_6$ alkyl, $R^{15}$-phenyl, $R^{15}$-benzyl, $-CF_3$ and $-C_2F_5$;

$R^6$ and $R^8$ are independently selected from the group consisting of $R^5$, $-(C(R^9)(R^{10}))_n-OR^{11}$, $-(C(R^9)(R^{10}))_n13$ $NR^{11}R^{12}$, $-(C(R^9)(R^{10}))_nSH$, $-(C(R^9)(R^{10}))_n-S(O)_eR^{13}$, $-(C(R^9)(R^{10}))_n-OC(O) CO_2R^{11}$, $-(C(R^9)(R^{10}))_n-OC(O)R^{11}$, $-(C(R^9)(R^{10}))_n-CONR^{11}R^{12}$, $-(C(R^9)(R^{10}))_n-COR^{11}$ and $-(C(R^9)(R^{10}))_n-NR^{11}C(O)R^{12}$, provided that when Q is a heteroatom, $R^6$ and $R^8$ cannot be $-OR^{11}$, $-OC(O)R^{11}$, $-N(R^{11})COR^{12}$, $-NR^{11}R^{12}$, $-SH$ or $-S(O)_eR^{13}$ on adjacent carbon atoms;

$R^{10}$ is independently selected from the group consisting of hydrogen and $C_1$–$C_6$ alkyl;

$R^{13}$ is independently selected form the group consisting of $C_1$–$C_6$ alkyl; $R^{15}$-phenyl, $R^{15}$benzyl, $-CF_3$ and $-C_2F_5$;

$R^{15}$ is hydrogen, $C_1$–$C_6$ alkyl, $C_1$–$C_6$ alkoxy or halogeno;

Q is a bond, —C(O)—, —$NR^{17}$—, —$(C(R^9)(R^{10}))$—, —O—, —$S(O)_e$—, —$C(X)NR^{11}$—, —$N(R^{11})C(X)$—, —$N(R^{11})SO_2$—, —$SO_2N(R^{11})$— or —$N^+(R^{11})(R^{17})$—;

$R^{16}$ and $R^{17}$ are independently selected from the group consisting of hydrogen, $C_1$–$C_6$ alkyl, —$S(O)_eR^{13}$, —$COR^{11}$, —$(CH_2)_m$—$CO_2R^{13}$, —$CONR^{11}R^{12}$, alkenyl, —$R^{15}$-phenyl and $R^{15}$-benzyl;

X is =O, =S or =$N(R^{12})$;

$Y^1$ is —$(C(R^9)(R^{10}))_m$—, —G—$(C(R^9)(R^{10}))_m$— or —$(C(R^9)(R^{10}))_m$—G—;

G is

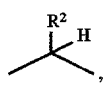

provided that when m is 0, $R^2$ is H, $C_1$–$C_6$ alkyl, —$CF_3$, —$C_2F_5$, —$COR^{11}$, —$CO_2R^{11}$, —$CON(R^{11})(R^{12})$, $R^{15}$-phenyl or $R^{15}$-benzyl;

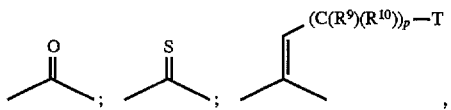

provided that when p is 0, T is not OH or —$NR^{11}R^{12}$;

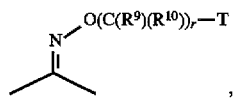

provided that when r is 1, T is not $OR^{11}$ or —$NR^{11}R^{12}$; or

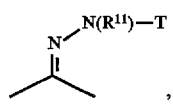

provided T is not —$OR^{11}$, —$N(R^{11})(R^{12})$, —$S(O)_eR^{13}$, —$NR^{11}CO_2R^{13}$, —$NR^{11}COR^{12}$, —$NR^{11}CON(R^{12})(R^{14})$ or —$OC(O)N(R^{11})(R^{12})$;

T is H, $R^{15}$-aryl, $R^{15}$-heterocycloalkyl, $R^{15}$-heteroaryl, $R^{15}$-cycloalkyl, —$OR^{11}$, —$N(R^{11})(R^{12})$, —$COR^{11}$, —$CO_2R^{11}$, —$CON(R^{11})(R^{12})$, —$S(O)_eR^{13}$, —$NR^{11}CO_2R^{13}$, —$NR^{11}COR^{12}$, —$NR^{11}CON(R^{12})(R^{14})$ or —$OC(O)N(R^{11})(R^{12})$;

J is a bond, —$S(O)_e$—, —O— or —$N(Z^2)$—, —$N(Z^2)C(O)$— or —$N(Z^2)C(S)$—; and when G is —$C(R^2)H$—, J can also be —$N(Z^2)C(O)O$— or —$OC(O)N(Z^2)$—;

$Y^2$ is —$(C(R^9)(R^{10}))_m$—;

$Z^1$ is H, $C_1$–$C_6$ alkyl, $R^{15}$-phenyl, $R^{15}$-benzyl, —$CF_3$, —$C_2F_5$, —$NR^{11}R^{12}$, —$OR^{11}$ or $SR^{11}$; $Z^2$ is H, $C_1$–$C_6$ alkyl, $R^{15}$-phenyl, $R^{15}$-benzyl, —$CF_3$ or —$C_2F_5$; provided that when $Y^1$ is —$(C(R^9)(R^{10}))_m$— and m is 0, $Z^1$ is not —$NR^{11}R^{12}$, —$OR^{11}$ or —$SR^{11}$; or $Z^1$ and $Z^2$ together are —$(C(R^9)(R^{10}))_u$—, wherein u is 1 to 4, and wherein with the atoms to which they are attached, form a 4 to 8 membered ring;

e and n are independently 0, 1 or 2;

m and p are independently 0, 1, 2 or 3; and r and s are independently 1, 2, 3 or 4.

Preferred are compounds of formula I wherein W is $R^4$-cycloakyl, $R^4$-aryl or $R^4$-heteroaryl. Preferred $R^1$, $R^2$, $R^3$ and $R^4$ substituents are H, halogeno, $C_1$–$C_6$ alkyl, —$CF_3$, —$OR^{11}$, —$COR^{11}$, —$CO_2R^{11}$, —$CON(R^{11})(R^{12})$ and —$N(R^{11})(R^{12})$. $R^5$, $R^7$, $R^9$, $R^{11}$, $R^{12}$ and $R^{14}$ are preferably independently H, $C_1$–$C_6$ alkyl or —$CF_3$. $R^6$ and $R^8$ are preferably independently hydrogen, —$(C(R^9)(R^{10}))_n$—$OR^{11}$, —$(C(R^9)(R^{10}))_n$—$NR^{11}R^{12}$, —$(C(R^9)(R^{10}))_n$—SH—, $(C(R^9)(R^{10}))_n$—$S(O)_eR^{13}$, —$(C(R^9)(R^{10}))_n$—$CO_2R^{11}$, —$(C(R^9)(R^{10}))_n$—$CONR^{11}R^{12}$ or —$(C(R^9)(R^{10}))_n$—$COR^{11}$; more preferably, $R^6$ and $R^8$ are each hydrogen or $R^8$ is hydrogen and $R^6$ is —$(C(R^9)(R^{10}))_n$—$CO_2R^{11}$. $R^{13}$ is preferably $C_1$–$C_6$ alkyl or $R^{15}$-phenyl. Q is preferably —$NR^{17}$—, —O— or —$S(O)_e$—, with —$NR^{17}$— being more preferred. When Q is —$NR^{17}$—, $R^{17}$ is preferably hydrogen, $C_1$–$C_6$ alkyl or $C_2$–$C_6$ alkenyl.

E is preferably $R^3$-phenyl. $Z^1$ is preferably hydrogen, or $Z^1$ and $Z^2$ together are ethylene or propylene, and with the atoms to which they are attached form a 5- or 6-membered ring. $Y^1$ is preferably —$(C(R^9)(R^{10}))_m$ or —$(C(R^9)(R^{10}))_m$—G, wherein m is preferably 0 or 1. In the definition of $Y^2$, m is preferably 0 or 1. J is preferably —O—, —$N(Z^2)$— or —$N(Z^2)C(O)$—.

Preferred are compounds wherein $A^4$ is a bond. Also preferred are compounds wherein $A^1$, $A^2$, $A^3$ and $A^4$ comprise an indolyl ring. Preferred compounds of formula I comprise compounds wherein $A^1$, $A^2$, $A^3$ and $A^4$ comprise an indolyl ring, $R^5$ and $R^6$ are each hydrogen and Q is —$NR^{17}$—, that is, compounds having the partial structure

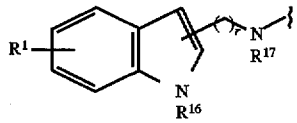

Also preferred are compounds of formula I wherein $R^7$ and $R^8$ are each hydrogen, s is 2, $Y^1$ is —$(C(R^9)(R^{10}))_m$— or —$(C(R^9)(R^{10}))_m$—G—, and J is —O—, —$N(Z^2)$— or —$N(Z^2)C(O)$—. Another group of preferred compounds is that wherein $Y^1$ is —$(C(R^9)(R^{10}))_m$— and J is —$N(Z^2)C(O)$—.

This invention also relates to the use of a compound of formula I in the treatment of asthma, cough, bronchospasm, inflammatory diseases such as arthritis, central nervous system conditions such as migraine and epilepsy, nociception, and various gastrointestinal disorders such as Crohn's disease.

In another aspect, the invention relates to a pharmaceutical composition comprising a compound of formula I in a pharmaceutically acceptable carrier. The invention also relates to the use of said pharmaceutical composition in the treatment of asthma, cough, bronchospasm, inflammatory diseases such as arthritis, migraine, nociception, and various gastrointestinal disorders such as Crohn's disease.

DETAILED DESCRIPTION

As used herein, the term "alkyl" means straight or branched alkyl chains. "Lower alkyl" refers to alkyl chains of 1–6 carbon atoms and, similarly, lower alkoxy refers to alkoxy chains of 1–6 carbon atoms.

"Alkenyl" means a straight or branched alkane chain of 2–6 carbon atoms having one double bond.

"Cycloalkyl" refers to cyclic alkyl groups of 3–6 carbon atoms.

"Aryl" means phenyl, naphthyl, indenyl, tetrahydronaphthyl, indanyl, anthracenyl or fluorenyl.

"Halogeno" refers to fluoro, chloro, bromo or iodo atoms.

"Heterocycloalkyl" refers to 4- to 6-membered saturated rings comprising 1 to 3 heteroatoms independently selected from the group consisting of —O—, —S— and —N($R^{16}$)—, with the remaining ring members being carbon. Examples of heterocycloalkyl rings are tetrahydrofuranyl, pyrrolidinyl, piperidinyl, morpholinyl, thiomorpholinyl and piperazinyl. $R^4$-heterocycloalkyl refers to such groups wherein substitutable ring carbon atoms have an $R^4$ substituent.

"Heteroaryl" refers to 5- to 10-membered single or benzofused aromatic rings comprising 1 to 4 heteroatoms independently selected from the group consisting of —O—, —S— and —N=, provided that the rings do not include adjacent oxygen and/or sulfur atoms. Examples of single-ring heteroaryl groups are pyridyl, isoxazolyl, oxadiazolyl, furanyl, pyrrolyl, thienyl, imidazolyl, pyrazolyl, tetrazolyl, thiazolyl, thiadiazolyl, pyrazinyl, pyrimidinyl, pyridazinyl and triazolyl. Examples of benzofused heteroaryl groups are indolyl, quinolinyl, thianaphthenyl and benzofurazanyl. N-oxides of nitrogen-containing heteroaryl groups are also included. All positional isomers are contemplated, e.g., 1-pyridyl, 2-pyridyl, 3-pyridyl and 4-pyridyl. $R^4$-heteroaryl refers to such groups wherein substitutable ring carbon atoms have an $R^4$ substituent.

Those skilled in the art will appreciate that the groups comprising $A^1$, $A^2$, $A^3$ and $A^4$ are shown in the above description without a free valence, but that one of $A^1$, $A^2$, $A^3$ or $A^4$ must have a free valence to bond to the —(C($R^5$)($R^6$))$_r$— group, that is, one of the $R^2$, $R^{2c}$, $R^{10}$ or $R^{16}$ substituents on one of $A^1$, $A^2$, $A^3$ or $A^4$ is replaced by a bond to the —(C($R^5$)($R^6$))$_r$— group.

The proviso in the definitions of $R^6$ and $R^8$ relating to compounds wherein Q is a heteroatom is intended to allow for —$OR^{11}$, —OC(O)$R^{11}$, —N($R^{11}$)COR$^{12}$, —NR$^{11}$R$^{12}$, —SH or —S(O)$_e$R$^{13}$ substitution on compounds wherein r and/or s is 2 or 3, as long as the carbon adjacent to Q is not substituted by those groups. The proviso that three adjacent A groups do not represent —C(O)—O—C(O)—, —S(O)—O—C(O)— or —S(O)—O—S(O)— is intended to eliminate unstable ring systems.

In the definition of Q, the group —N$^+$($R^{11}$)($R^{17}$)— refers to quaternary amine groups.

In the above definitions, wherein $R^5$, $R^7$, $R^9$, $R^{11}$, $R^{12}$ and $R^{14}$ are said to be independently selected from a group of substituents, we mean that $R^5$, $R^7$, $R^9$, $R^{11}$, $R^{12}$ and $R^{14}$ are independently selected, but also that where an $R^5$, $R^7$, $R^9$, $R^{11}$, $R^{12}$ or $R^{14}$ variable occurs more than once in a molecule, those occurrences are independently selected. Similarly, $R^1$, $R^3$, $R^4$ and the $R^2$ variables can be independently selected from a group of substituents, and where more than one of those variables is present, the substitutents are independently selected; those skilled in the art will recognize that the size and nature of the substituent(s) will affect the number of substituents which can be present.

Compounds of the invention can have at least one asymmetrical carbon atom and therefore all isomers, including diastereomers, enantiomers and rotational isomers are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of formula I.

Those skilled in the art will appreciate that for some compounds of formula I, one isomer will show greater pharmacological activity than other isomers.

Compounds of the invention have at least one amino group which can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

Compounds of formula I can be prepared using methods well known to those skilled in the art. Following are typical procedures for preparing various compounds; the skilled artisan will recognize that other procedures may be applicable, and that the procedures may be suitable modified to prepare other compounds within the scope of formula I.

Procedure A:

Compounds of formula I wherein —Q—(C($R^7$)($R^8$))$_s$— is —N($R^{11}$)CH$_2$CH$_2$—, $Z^1$ is a hydrogen, $Y^1$ is —CH$_2$—, and J is —N(CH$_3$)C(O)— can be prepared as shown in the following reaction scheme:

Step 1

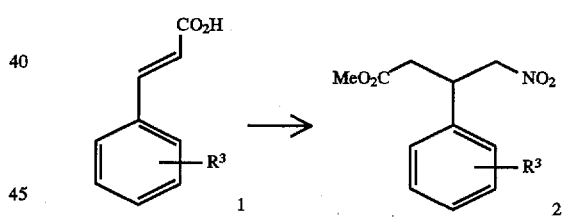

In step 1, a 3-($R^3$-phenyl)-2-propenoic acid (1) is treated with a lower alkyl alcohol such as CH$_3$OH in the presence of a suitable acid catalyst such as HCl in the range of 0° to 100° C. to give the corresponding ester. This ester is reacted with a nitroalkane such as CH$_3$NO$_2$ in the presence of a suitable base such as benzyltrimethylammonium hydroxide at a temperature range of 0° to 100° C. to give the desired compound 2.

Step 2

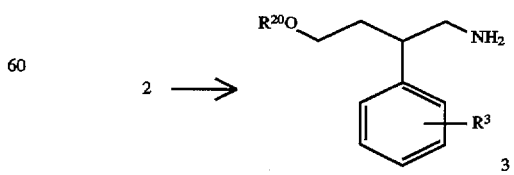

In step 2, compound 2 is reacted with a strong reducing agent such as LiAlH$_4$ or BH$_3$. DMS in an inert organic solvent such as THF, ether or benzene, preferably THF, at a temperature range from 0° to 80° C. The resulting amino alcohol is reacted with an electrophile such as a compound of formula $R^{20}L^1$, wherein $R^{20}$ is a suitable hydroxyl-protecting group such as $(R^{21})_3Si-$, wherein $R^{21}$ are independently selected lower alkyl groups (e.g., methyl, ethyl, isopropyl or t-butyl), and $L^1$ is a leaving group such as Cl or Br.

Step 3

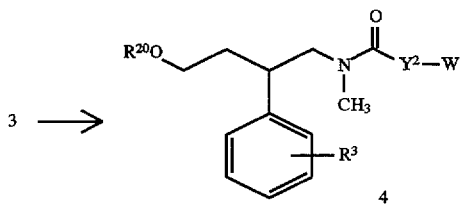

In step 3, amine 3 is acylated by standard procedures, for example by treatment with an acid chloride, $WY^2COCl$, in the presence of an amine base in an inert organic solvent such as $CH_2Cl_2$ or toluene, preferably $CH_2Cl_2$, at a temperature of from −10° to 50° C. Suitable bases include $(CH_3)_3N$, $Et_3N$ and pyridine, preferably $Et_3N$. Other coupling methods known to those skilled in the art, such as EDC coupling, may also be employed. The resulting amide is treated with a base such as NaH or LDA, in an inert organic solvent such as THF, ether, DMSO or DMF, preferably THF. The resulting anion is treated with an alkylating agent $R^{11}L$, wherein $R^{11}$ is as defined above and L is a suitable leaving group such as Cl, Br, I, triflate or mesylate; preferably $R^{11}L$ is $CH_3I$. The reactions are typically run at 0° to 50° C.

Step 4

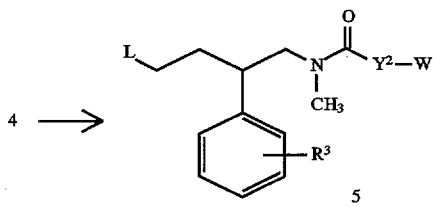

In step 4, the free hydroxyl group is regenerated by treatment of compound 4 with a fluoride reagent such as tetrabutylammonium fluoride, The hydroxyl group is converted to a suitable leaving group L, as defined above, preferably mesylate, The corresponding mesylate can be obtained by treatment with $CH_3SO_2Cl$ in a suitable solvent such as $CH_2Cl_2$ in the presence of a base such as $Et_3N$.

Step 5

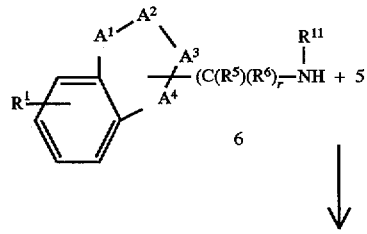

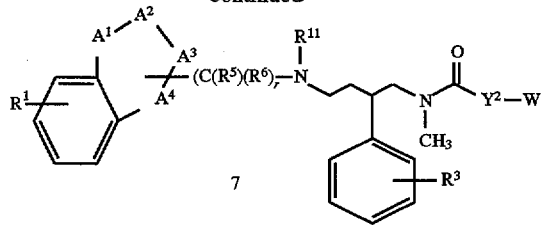

In step 5, compound 5 is treated with compound 6 in an inert solvent such as $CH_2Cl_2$, THF or DMF, preferably DMF, preferably with a catalytic amount of NaI, and preferably at temperatures from 20° to 80° C.

Procedure A1:

Step 1

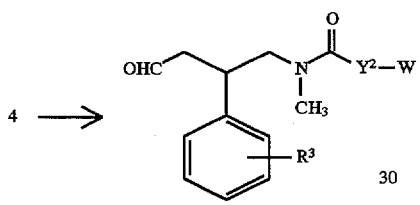

Alternatively to Procedure A, compound 4 is treated with a fluoride reagent such as tetrabutylammonium fluoride to regenerate the free hydroxyl group. The resulting compound is converted to aldehyde 30 by a suitable oxidation procedure, for example by the Swern procedure as described in *Tetrahedron*, 1978, 34, 1651.

Step 2

6+30→7

In step 2, compound 30 is reacted with an amine of formula 6 in an alcohol such as $CH_3$, $CH_3CH_2OH$ or more preferably $CF_3CH_2OH$, in the presence of a dehydrating agent such as molecular sieves and a reducing agent such as $NaBH_3CN$ or under hydrogenation conditions ($H_2/Pd/C$). A suitable temperature range is 0° to 60° C.

Procedure A2:

Step 1

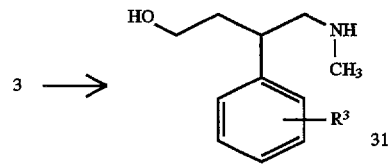

As another alternative to Procedure A, compound 3 is converted to the formamide by standard procedures, for example by treatment with ethylformate, preferably at a temperature from 30° to 60° C. The resulting formamide is treated with a suitable reducing reagent such as $BH_3.DMS$ or $AlH_3$, preferably $BH_3.DMS$. The resulting amine-borane complex and the silyl protecting group are hydrolyzed by treatment with aqueous acid such as HCl, preferably at a temperature from 50° to 100° C.

Step 2

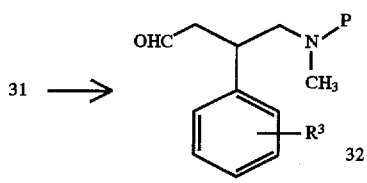

In step 2, the amino group in compound 31 is suitably protected such as by treatment with di-t-butyl dicarbonate to obtain the t-butyl carbamate. The hydroxyl group is converted to the aldehyde by a suitable oxidation procedure, for example by the Swern procedure.

Step 3
6 + 32 →

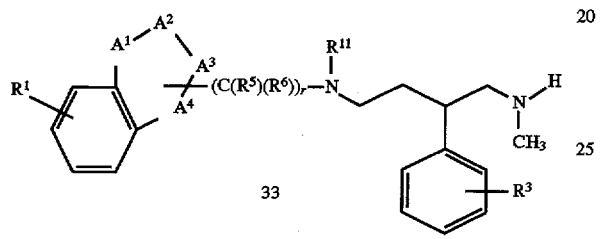

In step 3, compound 32 is reacted with an amine of formula 6 in manner such as that described in Procedure A1, Step 2. The free methylamino group is regenerated by treatment with acid such as trifluoroacetic acid or HCl in the presence of a suitable solvent such as $CH_2Cl_2$ or $CH_3OH$.

Step 4

33→7

In step 4, compound 33 is acylated by standard procedures, for example by treatment with an acid chloride, $WY^2COCl$, in the presence of an amine base in an inert organic solvent such as $CH_2Cl_2$ or toluene, preferably $CH_2Cl_2$, at a temperature of from −10° to 50° C. Suitable bases include $(CH_3)_3N$, $Et_3N$ and pyridine, preferably $Et_3N$. Other coupling methods known to those skilled in the art, such as EDC coupling, may also be employed.

Procedure B:

Compounds of formula I wherein —Q—$(C(R^7)(R^8))_s$— is —$N(R^{11})CH_2CH_2$—, $Z^1$ is hydrogen, $Y^1$ is —C(OH)H—, and J is —O— can be prepared as shown in the following reaction scheme:

Step 1

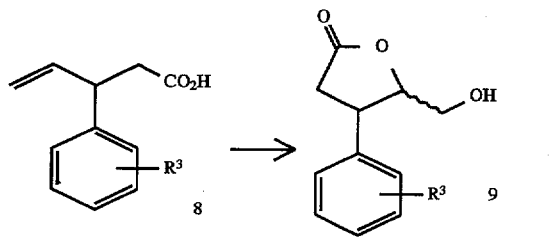

In step 1, the 3-($R^3$-phenyl)-4-pentenoic acid 8, is reacted with an oxidizing agent such as dimethyl dioxirane or m-CPBA in an inert organic solvent such as $CH_2Cl_2$ or toluene, preferably at reaction temperatures from 0° to 60° C. An acidic catalyst such as Amberlyst-15 or formic acid is added to give the desired lactone 9.

Step 2

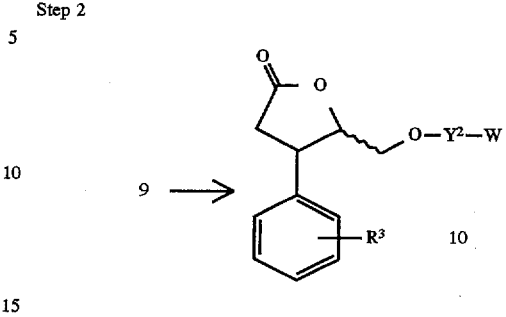

In step 2, lactone 10 is reacted with an electrophile $L^1$—$Y^2$—W wherein $L^1$ is a leaving group such as Cl or Br. The reaction is carried out in the presence of a silver salt such as $Ag_2O$ in an organic solvent such as DMF or THF, most preferably DMF, at a temperature of 0° to about 50° C.

Step 3

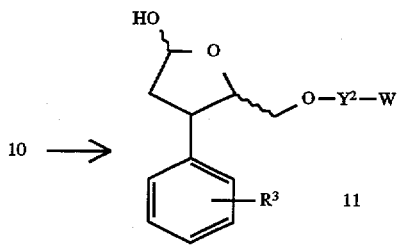

In step 3, compound 10 is dissolved in an inert organic solvent such as $CH_2Cl_2$, THF or toluene, preferably $CH_2Cl_2$, and treated with a reducing agent such as DIBAL-H at temperatures from about −78° C. to room temperature.

Step 4

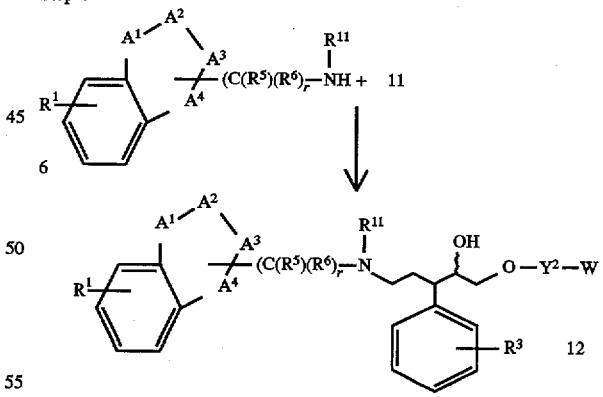

In Step 4, compound 11 is reacted with an amine of formula 6 in a manner such as that described in Procedure A1, Step 2.

Procedure C:

Compounds of formula I wherein —Q—$(C(R^7)(R^8))_s$— is —$N(R^{11})(CH_2)_s$— and s is 2 or 3, $Z^1$ is hydrogen, $Y^1$ is —C(=NO$(C(R^9)(R^{10}))_rT)(CH_2)_m$— and m is 1 to 3, and J is —O— can be prepared as shown in the following reaction scheme:

11

Step 1

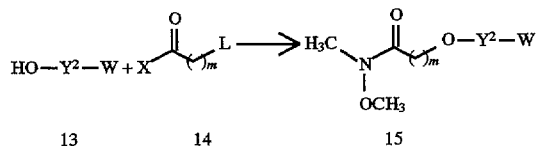

In step 1, an alcohol with the structure 13 is treated with a base such a NaH or LDA, preferably NaH, in an inert solvent such as THF or DMF. The resulting alkoxide is added to an electrophile such as a compound of formula 14 wherein m is 1, 2 or 3 and L is a leaving group as defined above, preferably Br, and X is —N(CH$_3$)OCH$_3$ or —Oalkyl. Preferable reaction temperatures range from –20° to 50° C. When X is Oalkyl, it is then treated with HN(CH$_3$)OCH$_3$ and Al(CH$_3$)$_3$ in an inert organic solvent such as THF or toluene at a temperature of –20° to 40° C.

Step 2

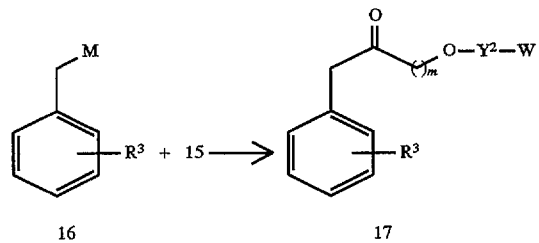

In step 2, compound 15 is treated with a reagent of formula 16 wherein M is Li, MgCl or MgBr, in an inert organic solvent such as THF or ether, at a temperature of –78° to 40° C.

Step 3

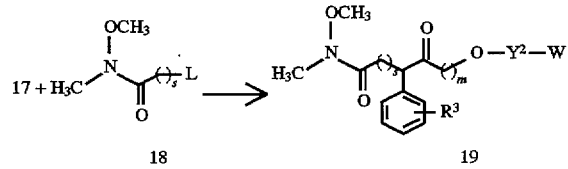

In step 3, compound 17 is treated with a suitable base such as NaN(TMS)$_2$ or LDA, preferably NaN(TMS)$_2$, in an inert organic solvent such as THF. The resulting anion is treated with a compound of formula 18 wherein s is 1 or 2 and L is a leaving group as defined above, in an inert organic solvent such as THF or ether at reaction temperatures ranging from –78° to 30° C.

Step 4

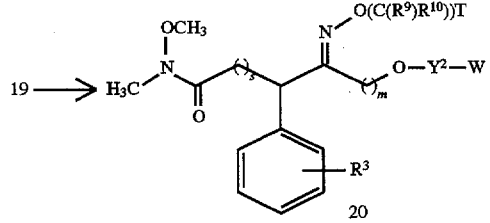

A compound of formula 19 is converted to the corresponding oxime of formula 20 by treating the ketone 19 with a hydroxylamine derivative of the formula H$_2$NO(C(R$^9$)(R$^{10}$))$_r$T, in a suitable organic solvent such as pyridine at a temperature of from 25° to 100° C. Alternatively, a low molecular weight alcohol (e.g. CH$_3$OH or CH$_3$CH$_2$OH) can be used as the solvent, in which case a base such as sodium acetate must be added.

Step 5

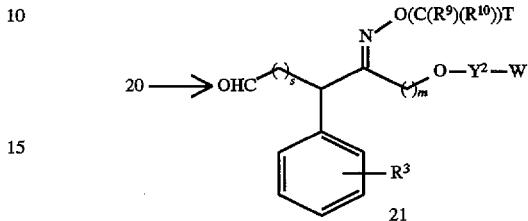

In step 5, compound 20 is treated with a reducing agent such as DIBAL-H in an inert organic solvent such as THF or CH$_2$Cl$_2$ at a temperature from –78° to –40° C.

Step 6

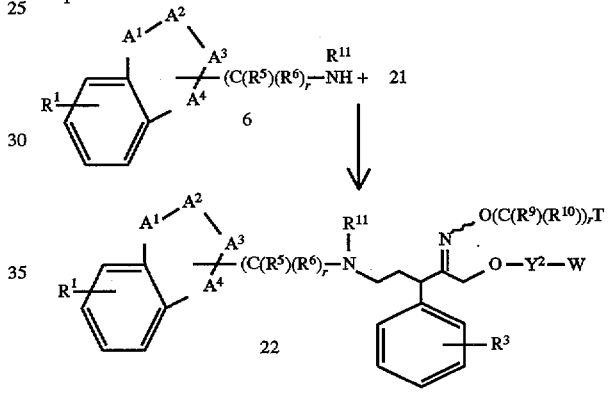

In Step 6, compound 21 is reacted with an amine of formula 6 in a manner such as that described i Procedure A1, Step 2.

Procedure D:

Compounds of formula I wherein —Q—(C(R$^7$)(R$^8$))$_s$— is —N(R$^{11}$)CH$_2$CH$_2$—, Z$^1$ is hydrogen, Y$^1$ is —CH$_2$C(O)—, and J is —N(CH$_3$)— can be prepared as shown in the following reaction scheme:

Step 1

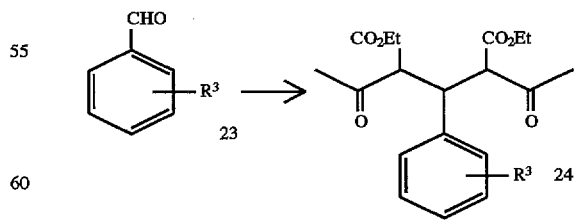

In step 1, an aldehyde of formula 23 is reacted with ethylacetoacetate in polar organic solvent such as CH$_3$CH$_2$OH in the presence a suitable base, e.g., piperidine, at a temperature of 10° to 50° C.

Step 2

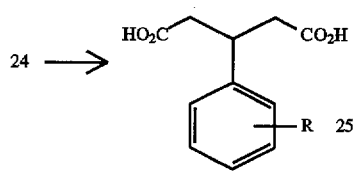

In step 2, compound 24 is converted to the diacid compound of formula 25 by treatment with a strong base such as NaOH in an aqueous alcoholic solvent such as $CH_3CH_2OH$ at a temperature from 60° to 100° C., preferably at the reflux temperature of the solvent.

Step 3

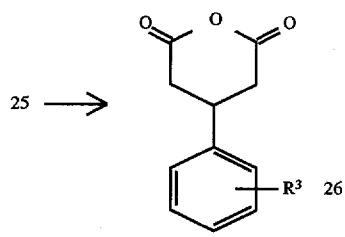

In step 3, compound 25 is treated with a dehydrating reagent such as $CH_3COCl$ or DCC, preferably $CH_3COCl$.

Step 4

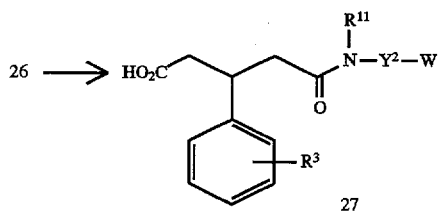

Treatment of anhydride 26 with an amine of the formula $W—Y^2—NHR^{11}$ in a suitable solvent such as $CH_2Cl_2$ in the presence of a suitable base such as $Et_3N$ or N,N-dimethylamino-pyridine gives acid 27.

Step 5

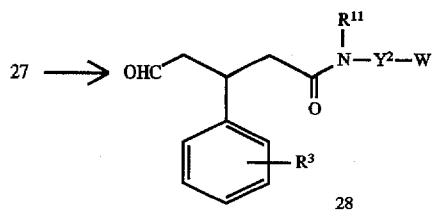

Acid 27 is converted to the alcohol by a suitable reduction procedure. For example, a compound 27 a treated with 1,1'-carbonyldiimidazole in an organic solvent such as ethyl acetate in the presence of a suitable base such as N,N-dimethylaminopyridine followed by treatment with aqueous $NaBH_4$. The alcohol is converted to the aldehyde 28 by a suitable oxidation procedure.

Step 6

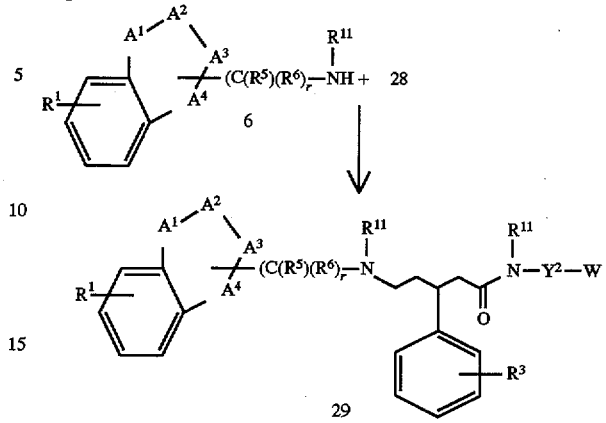

In Step 6, compound 28 is reacted with an amine of formula in a manner such as that described in Procedure A1, Step 2.

Procedure E:

Compounds of formula I wherein $—Q—(C(R^7)(R^8))_s—$ is $—N(R^{11})CH_2CH_2—$, $Y^1$ is $—CH_2—$, J is $—N(Z^2)CO—$ and $Z^1$ and $Z^2$ together are $—CH_2CH_2—$ can be prepared as shown in the following reaction scheme:

Step 1

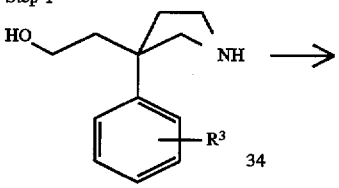

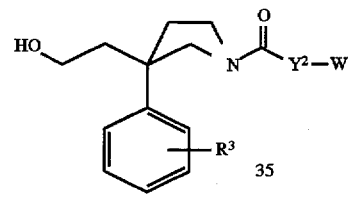

In step 1, 3-($R^3$-phenyl)-3-(2-hydroxyethyl)-pyrrolidine 34 (which can be obtained by the procedure described in T. B. Burkholder et al. *Bioorg. & Med. Chem. Let.* 6, (1996), p. 951) is acylated by standard procedures as described in Procedure A2, Step 4.

Step 2

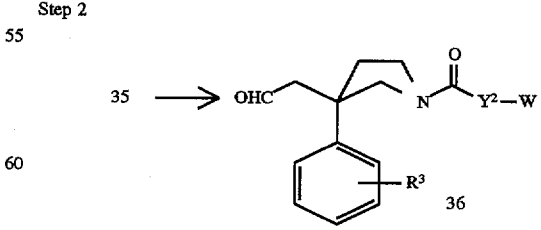

In step 2, compound 35 is converted to aldehyde 36 by a suitable oxidation procedure, for example by the Swern procedure.

Step 3
6 + 36 ⟶

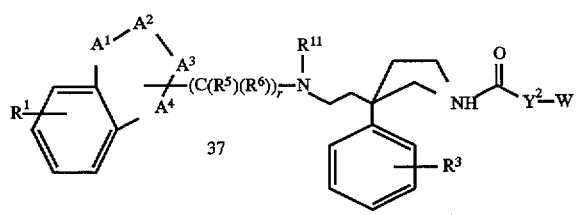

In step 3, compound 36 is reacted with an amine of formula 6 in a procedure such as described in Procedure A1, Step 2.

Reactive groups not involved in the above processes can be protected during the reactions with conventional protecting groups which can be removed by standard procedures after the reaction. The following Table 1 shows some typical protecting groups:

TABLE 1

| Group to be Protected | Group to be Protected and Protecting Group |
|---|---|
| —COOH | —COOalkyl, —COObenzyl, —COOphenyl |
| \NH/ | \NCOalkyl/, \NCObenzyl/, \NCOphenyl/, \NCH₂OCH₂CH₂Si(CH₃)₃/  \NC(O)OC(CH₃)₃/, \N-benzyl/, \NSi(CH₃)₃/, \NSi—C(CH₃)₃ with CH₃/CH₃ |
| —NH₂ | —N(succinimide) |
| —OH | —OCH₃, —OCH₂OCH₃, —OSi(CH₃)₃, —OSi—C(CH₃)₃ with CH₃/CH₃, or —OCH₂phenyl |

Compounds of formula I have been found to be antagonists of NK$_1$ and/or NK$_2$ and/or NK$_3$ receptors, and are therefore useful in treating conditions caused or aggravated by the activity of said receptors.

The present invention also relates to a pharmaceutical composition comprising a compound of formula I and a pharmaceutically acceptable carrier. Compounds of this invention can be administered in conventional oral dosage forms such as capsules, tablets, powders, cachets, suspensions or solutions, or in injectable dosage forms such as solutions, suspensions, or powders for reconstitution. The pharmaceutical compositions can be prepared with conventional excipients and additives, using well known pharmaceutical formulation techniques. Pharmaceutically acceptable excipients and additives include non-toxic and chemically compatibile fillers, binders, disintegrants, buffers, preservatives, anti-oxidants, lubricants, flavorings, thickeners, coloring agents, emulsifiers and the like.

The daily dose of a compound of formula I for treating asthma, cough, bronchspasm, inflammatory diseases, migraine, nociception and gastrointestinal disorders is about 0.1 mg to about 20 mg/kg of body weight per day, preferably about 0.5 to about 15 mg/kg. For an average body weight of 70 kg, the dosage range is therefore from about 1 to about 1500 mg of drug per day, preferably about 50 to about 200 mg, more preferably about 50 to about 500 mg/kg per day, given in a single dose or 2–4 divided doses. The exact dose, however, is determined by the attending clinician and is dependent on the potency of the compound administered, the age, weight, condition and response of the patient.

Following are examples of preparing starting materials and compounds of formula I.

EXAMPLE 1

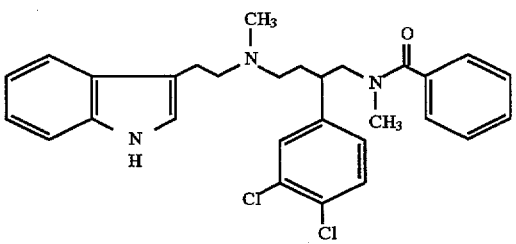

Step 1:

Reflux a solution of 3-(3,4-dichlorophenyl)-2-propenoic acid (26.02 g, 0.12 mol), CH$_3$OH (500 mL) and saturated methanolic HCl (5.0 mL) for 14 h. Cool to precipitate white crystals and collect by filtration to give 22.6 g of the methyl ester product (0.098 mol, 82%). Concentrate the filtrate and purify on a short silica gel column, eluting with 3:1 hexane: EtOAc to obtain an additional 4.43 g of the methyl ester (0.019 mol, 16%).

Step 2:

Treat the product of Step 1 (25.0 g, 0.108 mol) with 40% methanolic benzyltrimethylammonium hydroxide (9.3 mL, 22 mmol) and CH$_3$NO$_2$ (210 mL) and heat at 80° C. for 1.5 h. Dilute the reaction mixture with diethyl ether (Et$_2$O) (1 L), wash with 1N HCl (400 mL and 100 mL) and brine (500 mL), dry with MgSO$_4$ and concentrate. Chromatograph on silica gel, eluting with 3:1 hexane:EtOAc, to obtain 31.0 g of methyl 3-(3,4-dichlorophenyl)-4-nitrobutyrate (0.106 mol, 98%).

Step 3:

To a 1M Et$_2$O solution of LiAlH$_4$ (200 mL, 200 mmol) at 0° C., slowly add the product of Step 2 (14.35 g, 49.1 mmol) dissolved in tetrahydrofuran (THF) (100 mL). Allow the reaction mixture to warm to room temperature and stir for 45 min. After recooling to 0° C., quench the excess LiAlH$_4$ by the careful addition of aqueous saturated Na$_2$SO$_4$ (20 mL). Dry the solution with Na$_2$SO$_4$ and filter. Wash the lithium salts with Et$_2$O (3×300 mL). Concentrate the combined filtrates to give 8.65 g of 4-amino-3-(3,4-dichlorophenyl)-butanol as a white solid (36.9 mmol, 75%).

Step 4:

Treat a solution of the amino alcohol from Step 3 (8.13 g, 34.7 mmol) and imidazole (3.56 g, 52.3 mmol) in CH$_2$Cl$_2$ (350 mL) with tert-butyldimethylsilyl chloride (7.84 g, 52.0 mmol). After stirring for 1 h, wash the reaction with 0.1N HCl (350 mL) and extract the aqueous layer with CH₂Cl₂ (100 mL). Wash the combined organic layers with saturated NaHCO₃ (200 mL) and brine (200 mL), dry with K₂CO₃, and concentrate to give 11.4 g of the silylated product as a pale yellow viscous liquid (34.2 mmol, 98%).

Step 5:

Treat the amine from step 4 (15.3 g, 44 mmol) in CH₂Cl₂ (250 mL) with triethyl amine (Et₃N) (13 mL, 93 mmol) and benzoyl chloride (8.0 mL, 69 mmol). Stir at room temperature for 1.5 h, then wash the reaction mixture with H₂O (500 mL) and extract the aqueous layer with CH₂Cl₂ (2×100 mL). Wash the combined organic layers with 0.3N HCl (150 mL), saturated NaHCO₃ (150 mL) and brine (200 mL), dry with MgSO₄ and concentrate. Chromatograph the crude material on silica gel, eluting with 6:1 to 3:1 hexane:EtOAc to give 13.7 g of the benzamide (30 mmol, 69%).

Step 6:

Treat the product of step 5 (10.54 g, 23.3 mmol) in THF (170 mL) with 60% NaH (1.87 g, 47 mmol) followed by CH₃I (1.9 mL, 30.5 mmol). Heat the reaction mixture at 60° C. for 30 min and then partition between Et₂O (250 mL) and H₂O (500 mL). Extract the aqueous layer with Et₂O (500 mL), wash the combined organic layers with brine (250 mL), dry with MgSO₄ and concentrate to give 9.9 g of the methyl benzamide product as a colorless oil (21 mmol, 91%).

Step 7:

Treat the product of Step 6 (9.9 g, 21 mmol) in THF (125 mL) with a 1M THF solution of t-butylammonium fluoride (50 mL, 50 mmol) and stir for 4 h. Partition the reaction mixture between H₂O (200 mL) and Et₂O (100 mL). Extract the aqueous layer with Et₂O (2×100 mL), combine the organic layers and wash with brine (100 mL), dry with MgSO₄ and concentrate. Purify the crude product by recrystalization in CH₂Cl₂:hexane to give 5.5 g of the alcohol product as white crystals (15.6 mmol, 74.4%).

Step 8:

Stir the product of step 7 (1.37 g, 3.8 mmol) in CH₂Cl₂ (20 mL) with Et₃N (0.6 mL, 4.3 mmol) and C H₃SO₂Cl (0.32 mL, 4.1 mmol) for 45 min, then add the reaction mixture to 0.3N HCl (200 mL) and extract with CH₂Cl₂ (3×100 mL). Wash the combined organic layers with saturated NaHCO₃ (100 mL) and brine (100 mL), dry with MgSO₄ and concentrate to obtain 1.49 g of the methanesulfonate ester as a colorless viscous oil (3.47 mmol, 89%).

Step 9:

Heat the product of step 8 (0.499 g, 1.16 mmol) in DMF (5 mL) with Nω-methyl tryptamine (0.241 g, 1.38 mmol) and NaI (16.4 mg, 0.11 mmol) at 50° C. for 38 h. Add the reaction mixture to saturated NaHCO₃ (100 mL) and extract with CH₂Cl₂ (3×40 mL), wash the combined organic layers with brine (80 mL), dry with MgSO₄ and concentrate. Chromatograph on silica gel, eluting with 20:1:0.1 to 13:1:0.1 CH₂Cl₂:MeOH:NH₃ (aq.), gave 413 mg of the title compound as a white foam (0.81 mmol, 70%). HRMS (FAB, M+H⁺): m/e calc'd for [C₂₉H₃₂Cl₂N₃O]⁺ 508.1922; found 508.1929.

EXAMPLE 2

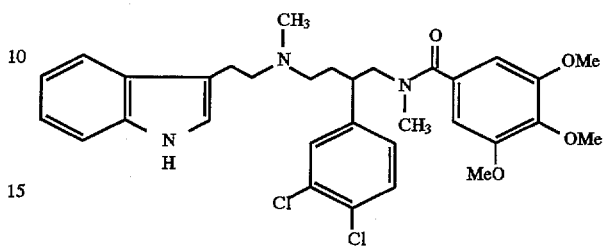

Step 1:

To a 0° C. solution of the product of Example 1, Step 4 (8.0 g, 22.9 mmol) in DMF, add 4-methylmorpholine (NMM) (2.5 mL, 22.9 mmol), 1-(3-dimethylaminopropyl)-3-ethylcarbodiimide hydrochloride (6.5 g, 34.4 mmol), 1-hydroxybenzotriazole hydrate (HOBT) (3.0 g, 22.9 mmol) and 3,4,5-trimethoxybenzoic acid (4.9 g, 22.9 mmol). Stir the reaction mixture at 0° C. for 30 min., then at room temperature overnight. Concentrate under high vacuum and resuspend the resulting material in H₂O and extract with EtOAc. Wash the combined organic layers with saturated NaHCO₃, dry with MgSO₄ and concentrate. Chromatograph the crude product on silica gel, eluting with 20:1 CH₂Cl₂:NH₃ saturated CH₃OH to give 9.0 g of amide as a light yellow solid (72%).

Steps 2–5:

Convert the product of Step 1 to the title compound using procedures similar to those described in Example 1, Steps 6 to 9. MS (FAB, M+H⁺): m/e 598; Analysis for C₃₂H₃₇Cl₂N₃O₄: Calc'd C, 64.21; H, 6.23; N, 7.20%; Found: C, 63.84; H, 6.37; N, 7.00.

EXAMPLE 2a

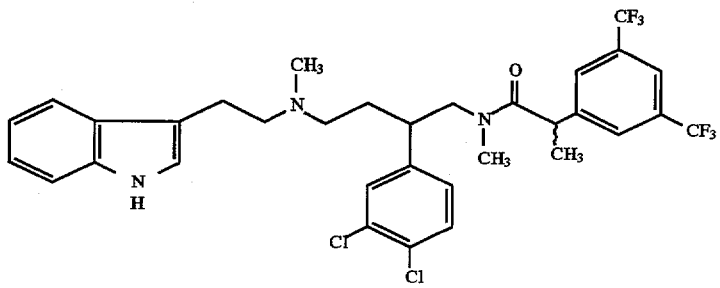

Using the procedure of Example 2, substitute 3,5-bis (trifluoromethyl)phenylacetic acid for 3,4,5- trimethoxybenzoic acid in step 1, and in step 2, methylate the benzylic position of the phenyl acetyl group and the amide position to obtain the title compound. MS (FAB, M+H⁺): m/e 672.

EXAMPLE 2b

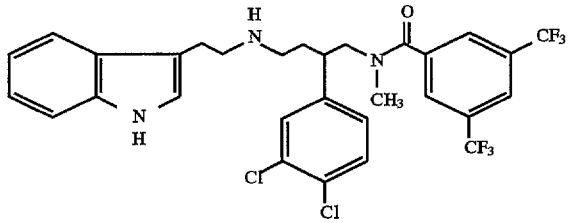

Using the procedure of Example 2, substitute 3,5-bis (trifluoromethyl)benzoic acid for 3,4,5-trimethoxybenzoic acid in step 1, and tryptamine for Nω-methyltryptamine in step 5 to obtain the title compound. HRMS (FAB, M+H⁺): m/e calc'd for $[C_{30}H_{28}N_3OCl_2F_6]^+$ 630.1514; found 630.1513.

EXAMPLE 2c

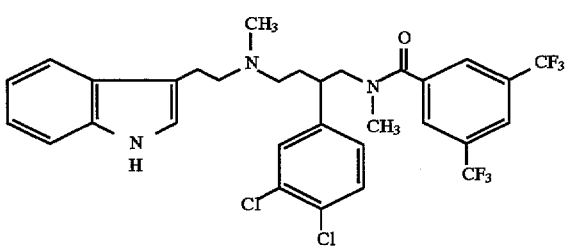

Using the procedure of Example 2, substitute 3,5-bis (trifluoromethyl)benzoic acid for 3,4,5-trimethoxybenzoic acid in step 1 to obtain the title compound.

EXAMPLE 2d

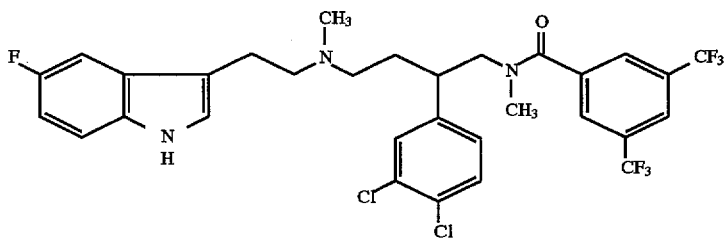

Using the procedure of Example 2c, substitute 5-fluoro-Nω-methyltryptamine for Nω-methyltryptamine in step 5 to obtain the title compound. HRMS (FAB, M+H⁺): m/e calc'd for $[C_{31}H_{29}N_3OCl_2F_7]^+$ 662.1576; found 662.1584.

EXAMPLE 2e

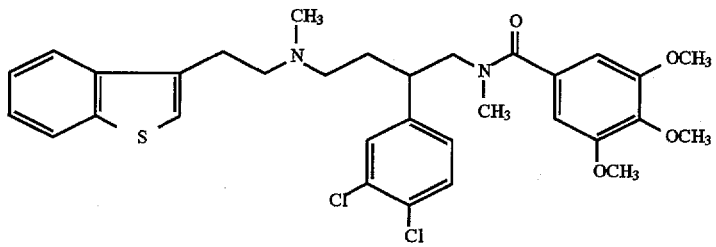

Using the procedure of Example 2, substitute N-methyl-3-(2-aminoethyl)benzothiophene for Nω-methyltryptamine in step 5 to obtain the title compound. HRMS (FAB, M+H$^+$): m/e calc'd for [C$_{32}$H$_{37}$N$_2$O$_4$Cl$_2$S]$^+$ 615.1851; found 615.1850.

EXAMPLE 3

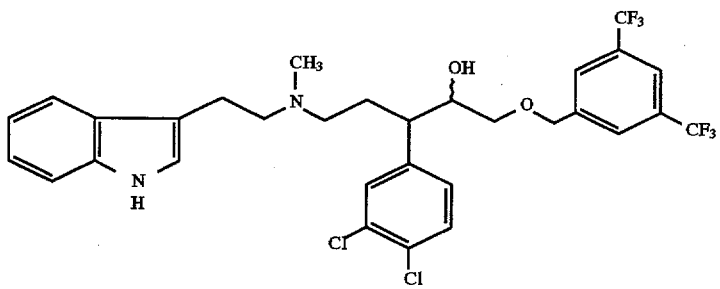

Step 1:

Cool a solution of 3-(3,4-dichlorophenyl)-2-propeneoic acid (100 g, 461 mmol) in dry DMF (500 mL) to 0° C. and treat with Cs$_2$CO$_3$ (100 g, 307 mmol). Stir the resulting off-white slurry for 15 min., then add CH$_3$I (33 mL, 530 mmol) via syringe. After 1 h, add additional DMF (250 mL) and stir the slurry for 14 h, then partition between ethyl acetate (EtOAc) (1.5 L) and half saturated aqueous NaHCO$_3$ (500 mL). Separate the organic layer and extract the aqueous layer with EtOAc (1 L, 500 mL). Wash the combined organic layers with half saturated aqueous NaHCO$_3$ (500 mL) and water (5×500 mL), then dry over Na$_2$SO$_4$ and concentrate to obtain methyl 3-(3,4-dichlorophenyl)-2-propenoate, 105.4 g (456 mmol, 99%, as light brown needles.

Step 2:

Treat a solution of the product of Step 1 (15 g, 65 mmol) in dry THF (250 mL) (kept cool in a large ambient temperature water bath) with DIBAL-H (140 mL, 140 mmol) over 30 min. Stir the resulting solution for 30 min at 23° C., pour into Et$_2$O (500 mL) and treat with water (5 mL), 15% NaOH (5 mL) and water (15 mL). Stir for 5 min, dilute the mixture with Et$_2$O (200 mL), add 15% NaOH (15 mL), then add MgSO$_4$ to obtain a colorless precipitate. Remove the aluminum salts by filtration through a coarse glass frit, wash the solids with Et$_2$O (1 L) and concentrate the filtrate in vacuo to give 3-(3,4-dichloro-phenyl)-2-propene-1-ol as an off-white solid, 13.2 g (65 mmol, 99%).

Step 3:

Combine a solution of the product of Step 2 (13.2 g, 65 mmol) in CH$_2$Cl$_2$ (250 mL) at 0° C. with pyridine (7.89 mL, 97.5 mmol) and dimethylaminopyridine (DMAP) (397 mg, 3.25 mmol), followed by acetyl chloride (6.48 mL, 74.7 mmol). Allow the mixture to warm to 23° C., pour into 1M HCl (100 mL) and wash the resulting organic layer with 1M HCl (100 mL) followed by water (5×100 mL; pH=6.5–7). Dry the organic layer over Na$_2$SO$_4$ and concentrate, providing 3-(3,4-dichloro-phenyl)-2-propene-1-ol acetate as a colorless oil, 15.4 g (62.9 mmol, 97%).

Step 4:

Treat a solution of the product of Step 3 (15 g, 61 mmol, dried by azeotropic distillation with toluene, 1×50 mL) in dry THF (250 mL) at −78° C. with chlorotriethylsilane (20.2 mL, 120 mmol), rapidly followed by the addition of 0.5M toluene solution of potassium bis(trimethylsilyl)amide (183 mL, 91.5 mmol) via addition funnel over 50 min. Allow the mixture to warm to 23° C., then heat to reflux for 3 h. Allow the solution to gradually cool overnight, then quench with saturated NH$_4$Cl (150 mL). Stir the resulting mixture vigorously for 3 h, treat with 1M HCl (150 mL) and extract with Et$_2$O (500 mL). Extract the aqueous layer with Et$_2$O (400 mL) and wash the combined organic layers with 300 mL of 5% NaOH followed by 8×150 mL of 5% NaOH. Cool the combined aqueous layers to 5° C. and carefully (temperature kept to 5°–10° C.) acidify with conc. HCl (ca 175 mL) to pH 1. Extract the aqueous layer with CH$_2$Cl$_2$ (2×800 mL), dry (Na$_2$SO$_4$) and concentrate to give 3-(3,4-di-chlorophenyl)-4-pentenoic acid as a faint yellow oil, 13.4 g (54.5 mmol, 89%).

Step 5:

Treat a solution of the product of Step 4 (5.0 g, 20.4 mmol) in dry CH$_2$Cl$_2$ (60 mL) with purified m-CPBA (7 g, 40 mmol) [wash 13 g of commercial 55% mCPBA in 250 mL of benzene with pH 7.4 buffer (5×30 mL), dry (Na$_2$SO$_4$) and concentrate to give about 9 g of pure m—CPBA]. After stirring for 48 h, add Amberlyst 15 (1.2 g) and stir the mixture for 8 h. Remove the Amberlyst by filtration through a medium porosity glass frit, rinsing with EtOAc. Wash the filtrate with 100 mL of saturated Na$_2$SO$_3$/NaHCO$_3$ (1:1), dry the resulting organic layer and concentrate in vacuo. Take up the crude product in hexane:CH$_2$Cl$_2$ (1:1) and filter to give 3.3 g (12.6 mmol, 62%) of a mixture of isomers (3:2, trans/cis) of the title compound as a colorless soft solid.

Concentrate the filtrate to give 2.0 g of a viscous oil which is purified by silica gel chromatography (column: 7×15 cm; solvent: hexane:EtOAc, 5:4 gradient to 1:1) to give 1.07 g (4.1 mmol, 20%) of the pure cis isomer of the title compound as an oil, total yield 4.3 g (16.47 mmol, 81%).
Step 6:

Treat a solution of 4-(3,4-dichlorophenyl)-dihydro-5-(hydroxymethyl) 2(3H)-furanone (3.3 g, 12.6 mmol, 3:2 ratio of stereoisomers by NMR) in dry DMF(10 mL) with 3,5-bistrifluoromethylbenzyl bromide (5.9 mL, 32.2 mmol) followed by Ag$_2$O (5.8 g, 25.3 mmol); wrap the vessel in foil and stir for 2.5 d. Apply the crude material to a pad of silica gel (10 cm×4 cm) packed with hexane:EtOAc (1:1), washing the pad with the same solvent until no further product is eluted as shown by TLC; concentrate the resulting filtrate in vacuo to give the crude product as a solid (10 g). Dissolve the crude was dissolved in hexane:EtOAc (4:1) and purify by silica gel chromatography (column: 7.5×19; solvent: hexane:EtOAc, 4:1) to give 3.33 g (6.8 mmol, 54%) of isomer (trans)-[[[(3,5-bis(trifluoromethyl)phenyl]methoxy] methyl]-4-(3,4-dichlorophenyl)-dihydro-2(3H)-furanone and 1.08 g (2.2 mmol, 17%) of the corresponding cis isomer for a total yield of 71%.

Trans isomer: HRMS (FAB, M+H$^+$): m/e calc'd for [C$_{20}$H$_{15}$O$_3$Cl$_2$F$_6$]$^+$: 487.0302, found 487.0312.

Cis isomer: HRMS (FAB, M+H$^+$): m/e calc'd for [C$_{20}$H$_{15}$Cl$_2$F$_6$O$_3$]$^+$: 487.0302, found 487.0297.
Step 7:

Cool a solution of the cis isomer of Step 6 (2.1 g, 4.31 mmol) in dry CH$_2$Cl$_2$ (50 mL) to −78° C. and treat with DIBAL-H (5.1 mL, 5.1 mmol; 1M in CH$_2$Cl$_2$). Stir for 2 h at −78° C., then treat the solution with NaF (905 mg 22 mmol) and water (400 μL, 22 mmol, 5 eq). Allow the suspension to warm to 23° C. and stir for 45 min., dilute the mixture with ET$_2$O (50 mL) and filter through a pad of silica gel (6.5 cm×2 cm; 150 mL vacuum glass frit) packed with hexane:EtOAc (1:1)), washing the pad with hexane:EtOAc (1:1) until no further product is evident as shown by TLC. Concentrate the filtrate to give 1.92 g (3.86 mmol, 91%) of the title compound as a foam which was used without further purification in the next step.
Step 8:

Stir a suspension of the lactol of Step 7 (1.03 g, 2.1 mmol), Nω-methyl tryptamine (0.73 g, 4.2 mmol) and 3A molecular sieves (1.7 g) in CF$_3$CH$_2$OH (5.0 mL) for 1 h, add NaCNBH$_3$ (0.26 g, 4.2 mmol) and stir the reaction mixture over the weekend, then concentrate. Chromatograph the residue on silica gel, eluting with 20:1 CH$_2$Cl$_2$/CH$_3$OH (saturated with ammonia) to give 0.809 g of the desired compound as a white solid (60%). MS (FAB, M+H$^+$): m/e 647.

EXAMPLE 4

Step 1:

Combine 3,5-bis(triflouromethyl)benzyl alcohol (25.0 g, 0.103 mol) in THF (50 mL) with 60% NaH (4.14 g, 0.104 mol) and stir for 30 min. Transfer the resulting alkoxide mixture via cannula over 30 min to a solution of methylbromoacetate (11.8 mL, 0.125 mol) in THF (250 mL). Stir the reaction mixture for 18 h and add to 0.3N HCl (300 mL). Separate the organic layer and extract the aqueous layer with EtOAc (2×150 mL). Wash the combined organic layers with brine (200 mL), dry with MgSO$_4$ and concentrate. Chromatograph on silica gel, eluting with 10:1 hexane: EtOAc, to give the desired product as a colorless liquid (26.1 g, 80%).
Step 2:

Combine a suspension of N,O-dimethylhydroxylamine hydrochloride (19.5 g, 0.20 mol) in THF (350 mL) at 0° C. with AlMe$_3$ (100 mL, 0.20 mol, 2M in toluene) and allow to warm to room temperature for 30 min. Cool this mixture to 0° C., add the product of Step 1 (26.1 g, 82.7 mmol) dissolved in THF (140 mL) over 30 min., warm the mixture to room temperature and stir for 40 min. Cool the reaction mixture to 0° C., quench by the careful addition of 1N HCl (100 mL) and concentrate. Partition the residue between H$_2$O (250 mL) and CH$_2$Cl$_2$ (300 mL), extract the aqueous layer with CH$_2$Cl$_2$ (2×150 mL) dry the combined organic layers with MgSO$_4$ and concentrate. Chromatograph on silica gel, eluting with 3:1 hexane:EtOAc to give the product as a colorless liquid (28.1 g, 98%).
Step 3:

Treat a suspension of Mg (1.35 g, 55.6 mmol) in Et$_2$O (10 mL) maintained at 30° C. with a solution of α,3,4-trichlorotoluene (7.7 mL, 55.6 mmol) in Et$_2$O (45 mL) over 1 h and then stir for 30 min. Transfer the resulting solution via cannula over 30 min to a −78° C. solution of the product of Step 2 (9.56 g, 27.7 mmol) in Et$_2$O (350 mL) and warm the reaction mixture to room temperature over 1 h. Cool the reaction mixture to 0° C. and treat with HCl saturated CH$_3$OH (4 mL) and CH$_3$OH (100 mL), stir for 1 h and concentrate. Partition the residue between CH$_2$Cl$_2$ (300 mL), Et$_2$O (500 mL) and H$_2$O (250 mL), dry the organic layer with MgSO$_4$ and concentrate. Chromatograph on silica gel, eluting with 2:1 CH$_2$Cl$_2$: hexane, to give the product as a white solid (6.22 g, 50%).
Step 4:

To a solution of sodium bis(trimethylsilyl)amide (2.5 mmol) in THF (20 mL) at −78° C., add, dropwise, a solution of the product from Step 3 (1.11 g, 2.5 mmol) in THF (5 mL) over 15 min. Stir at −78° C. for 2 h and then add a solution of 2-bromo-N-methoxy-N-methylacetamide (455 mg, 2.5 mmol) in THF (5 mL) dropwise over 10 min. Allow the mixture to warm to room temperature over 1 h, then stir at room temperature for an additional 30 min. Add brine to the reaction mixture (2 mL) and concentrate. Partition the residue between CH$_2$Cl$_2$ (60 mL), Et$_2$O (90 mL) and H$_2$O

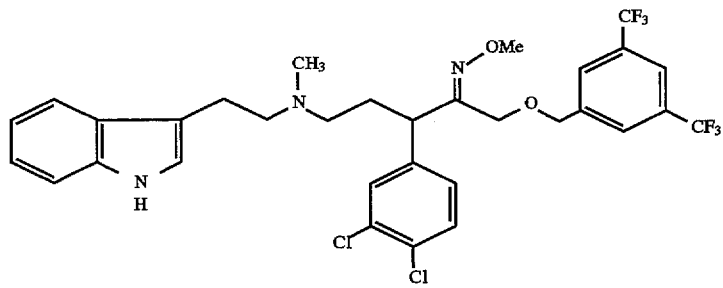

(30 mL). Wash the organic layer with brine (30 mL), dry with $Na_2SO_4$ and concentrate. Chromatograph on silica gel, eluting with $CH_2Cl_2$ to give the product as a colorless oil (800 mg, 56%).

Step 5:

Heat a mixture of the product of Step 4 (597 mg, 1.1 mmol), pyridine (10 mL) and methoxylamine hydrochloride (101.5 mg, 1.2 mmol) at 60° C. for 1 h and then concentrate. Chromatogra[ph on silica gel, eluting with 3:1 hexane:EtOAc to obtain the oxime (syn-isomer) as a colorless oil (442 mg, 70%). HRMS (FAB, M+H$^+$): m/e calc'd for $[C_{23}H_{22}Cl_2F_6N_2O_4]^+$: 575.0939, found 575.0932.

Step 6:

Treat the product of Step 5 (347 mg, 0.60 mmol) in THF (6 mL) at −78° C. with DIBAL-H (1.8 mL, 1.8 mmol, 1M in hexane) over 15 min. Add $H_2O$ (5 mL) and warm to room temperature; to this mixture, add NAF (0.2 g, 4.8 mmol) and stir for 20 min. Partition the reaction mixture between brine (25 mL) and $Et_2O$ (25 mL), dry the organic layer with $MgSO_4$ and concentrate to give the crude product (298 mg, 94%).

Step 7:

Treat the aldehyde of Step 6 (35 mg, 68 μmol) with Nω-methyl tryptamine (26.2 mg, 0.15 mmol), $CF_3CH_2OH$ (0.4 mL) and crushed 3Å molecular sieves (36 mg) and stir for 20 min. Add NaCNBH$_3$ (13 mg, 0.21 mol), stir for 14 h and concentrate. Chromatograph on silica gel, eluting with 10:1:0.1 $CH_2Cl_2$:MeOH:NH$_3$(aq) to give the title compound as a colorless oil (32 mg, 70%). MS (FAB, M+H$^+$): m/e calc'd 674.1776; found 674.1787.

EXAMPLE 5

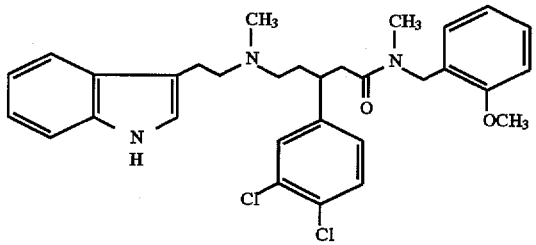

Step 1:

Combine 3,4-dichlorobenzaldehyde (100 g) in 95% $CH_3CH_2OH$ (120 mL) with ethylacetoacetate (146 mL) and stir until a homogenous solution is obtained. Treat this solution with piperidine (8 mL) and allow lo stand for 18 hours. Recrystallize the crude product from 95% ethanol to give diethyl-3,4-dichlorobenzal-bis-acetoacetate (230 g).

Step 2:

Reflux the product of Step 1 (155 g) in $CH_3CH_2OH$ (2 L) and 50% NaOH (2 l) for 4 hours. Add water (1 L) to the reaction mixture and remove approx. 1.5 L of solvent by distillation. Pour the remaining solution onto ice (1 Kg) and add sufficient HCl to adjust the pH to 1. Extract the resulting solution with EtOAc (3×1.5 L), dry the combined extracts over $MgSO_4$, filter and concentrate to give 100 g of 3-(3,4-dichlorophenyl)-glutaric acid.

Step 3:

Heat a combination of the product of Step 2 (100 g) and acetyl chloride (300 mL) at reflux for 5 hours. Cool the reaction mixture, azeotrope with toluene, and concentrate under reduced pressure. Slurry he residue with $Et_2O$ (250 mL) and filter to afford 3-(3,4-dichlorophenyl)-glutaric anhydride (86 g).

Step 4:

Sequentially treat the product of Step 3 (5.9 g) in $CH_2Cl_2$ (80 mL) at 0° C. with N-methyl-N-[2-(methoxyphenyl) methyl]amine (3.8 g), $Et_3N$ (3.5 mL) and DMAP (278 mg). Stir the mixture at 0° C. for 2 h, allow to warm to room temperature and stir for 20 h. Wash the reaction mixture with 1N HCl (1×100 mL) and brine (1×100 mL), dry the organic layers over $MgSO_4$, filter and concentrate to afford 3,4-dichloro-β-[2-[[(2-methoxy-phenyl)methyl]-methylamino]-2-oxoethyl] benzenepropanoic acid (9.3 g).

Step 5:

Treat the acid from Step 4 (9.3 g) in EtOAc (100 mL) with 1,1'-carbonyldiimidazole (4.62 g) and DMAP (345 mg), stir the resulting solution at room temperature for 15 min., then heat at 50° C. for 1 h. Cool the reaction mixture to 0° C. and treat with a solution of NaBH$_4$ (3.45 g) in $H_2O$ (50 mL), warm slowly to room temperature and stir for 12 h. Dilute the reaction mixture with EtOAc (250 mL) and wash with 1N HCl (1×100 mL) and $H_2O$ (1×100 mL), dry over $MgSO_4$, filter and concentrate under reduced pressure to yield a crude oil (13 g). Chromatograph on silica gel, eluting with 5% $CH_3OH/CH_2Cl_2$ to give 3,4-dichloro-β-(2-hydroxyethyl)-N-methyl-N-[(2-methoxyphenyl) methyl] benzenepropanamide (8.7 g). HRMS (FAB, M+H$^+$): m/e cal'd for $[C_{20}H_{24}NO_3Cl_2]^+$ 396.1133; found 396.1124.

Step 6:

Cool a solution of oxalyl chloride (1.43 mL) in $CH_2Cl_2$ (30 mL) to −78° C., add DMSO (2.32 mL) dropwise over 15 mins., stir for 15 min., then add a $CH_2Cl_2$ (20 mL) solution of the product of Step 5 (1.3 g) over 20 min. Stir the mixture for 30 min, treat with $Et_3N$ (9.2 mL) and stir for an additional 30 min. at −78° C., followed by 1.5 h at room temperature. Quench the reaction mixture with water and dilute with $CH_2Cl_2$ (100 mL). Separate the organic fraction, wash sequentially with 1N HCl (1×50 mL), sat. NaHCO$_3$ (1×50 mL) and brine (1×50 mL), dry over $MgSO_4$, filter and concentrate under reduced pressure to yield an oil. Chromatograph on silica gel, eluting with 50–100% EtOAc/ hexane to give 3,4-dichloro-β-(2-oxoethyl)-N-methyl-N-[(2-methoxyphenyl)methyl] benzenepropanamide (950 mg).

Step 7:

Sequentially treat the aldehyde of Step 6 (770 mg), in 2,2,2-trifluoroethanol (5 mL) with molecular sieves 3A (510 mg), N-ω-methyltryptamine (510 mg) and NaCNBH$_3$ (123 mg). Stir the resulting mixture at room temperature for 18 h., dilute the reaction mixture with EtOAc (50 mL) and filter through silica gel. Concentrate the resulting organic layer under reduced pressure to give the crude product as an oil. Chromatograph on silica gel, eluting with 10% MeOH/ $CH_2Cl_2$ gave the title compound (525 mg). HRMS (FAB, M+H$^+$): m/e cal'd for $[C_{21}H_{35}N_3O_2Cl_2]^+$ 552.2185; found: 552.2179.

EXAMPLE 6

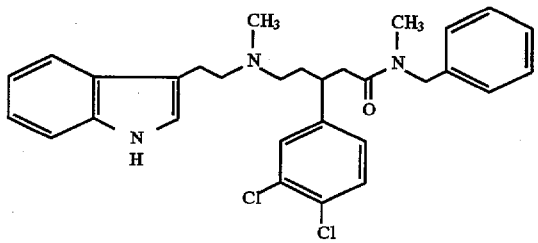

The compound of Example 6 is prepared by a procedure similar to that descruibed in Example 5 except using N-methyl-N-phenyl-methylamine in place of N-methyl-N-[2-(methoxyphenyl)methyl]amine. MS (FAB, M+H$^+$): m/e 522; Analysis for $C_{30}H_{33}Cl_2N_3O\cdot 0.5H_2O$: Found: C, 67.84; H, 6.43; N, 7.90; calc'd C, 67.79; H, 6.45; N, 7.91%.

EXAMPLE 7

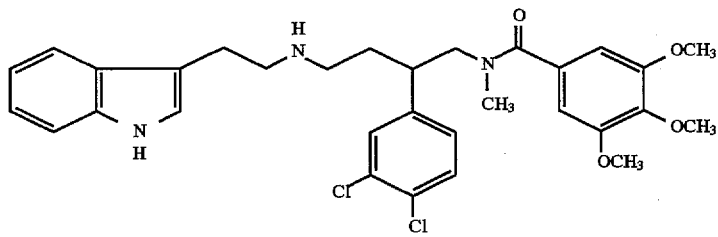

Step 1:

To a −55° C. solution of oxalyl chloride (2.25 mL, 25.8 mmol) in $CH_2Cl_2$ (45 mL), slowly add a solution of DMSO (2.4 mL, 33.8 mmol) in $CH_2Cl_2$ (45 mL) followed by a solution of the alcohol from Example 2, Step 3 (7.55 g, 17.1 mmol) in $CH_2Cl_2$ (90 mL). Stir for 30 min. at −55° C., add $Et_3N$ (9.2 mL, 66 mmol) and stir for 2 h at −55° C. Add 20% sat. $KHSO_4$ (75 mL) and $Et_2O$ (100 mL), warm to room temperature and stir for 30 min. Add to $Et_2O$ (225 mL) and remove the aqueous layer, wash with sat. $NaHCO_3$ (2×100 mL), $H_2O$ (100 mL) and brine (100 mL). Dry the solution with $MgSO_4$ and concentrate to give 7.36 g of desired aldehyde product as a white foam (16.7 mmol, 98%).

Step 2:

Treat a solution of the product from step 1 (2.48 g, 5.6 mmol), tryptamine (1.44 g, 9.0 mmol) and crushed 3A mol. sieves (1.66 g) in $CF_3CH_2OH$ (50 mL) with $NaCNBH_3$ (1.57 g, 25 mmol). Stir the reaction mixture for 30 min, filter and concentrate. Chromatograph the crude product on silica gel, eluting with 25:10:1 to 10:1:0.1 $CH_2Cl_2$:MeOH:$NH_3$ (aq.) to give 2.43 g of product as a white foam (4.16 mmol, 74%). MS (FAB, M+H$^+$): m/e 584.

EXAMPLE 7a

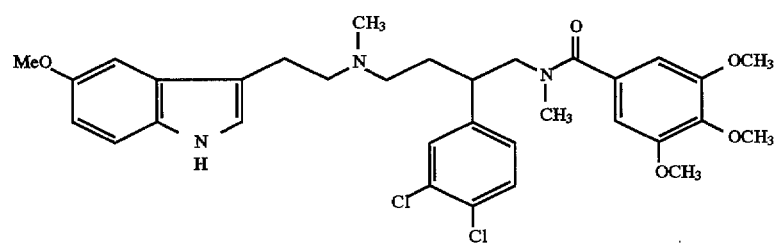

Using the procedure of Example 7, substitute 5-methoxy-Nω-methyltryptamine for Nω-methyltryptamine in step 2 to obtain the title compound. HRMS (FAB, M+H$^+$): m/e calc'd for $[C_{33}H_{40}N_3O_5Cl_2]^+$ 628.2345; found 28.2345.

EXAMPLE 7b

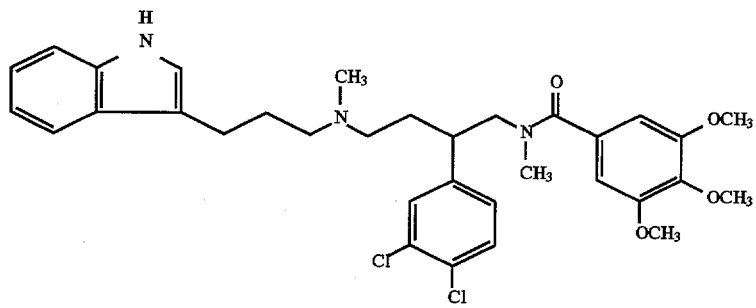

Using the procedure of Example 7, substitute 3-(N-methyl-3-aminopropyl)indole for Nω-methyltryptamine in step 2 to obtain the title compound. HRMS (FAB, M+H$^+$): m/e calc'd for $[C_{33}H_{40}N_3O_4Cl_2]^+$ 612.2396; found 612.2399.

EXAMPLE 7c

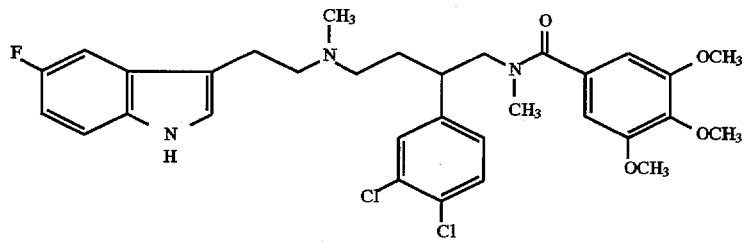

Using the procedure of Example 7, substitute 5-fluoro-Nω-methyltryptamine for Nω-methyltryptamine in step 2 to obtain the title compound. HRMS (FAB, M+H$^+$): m/e calc'd for $[C_{32}H_{37}N_3O_4Cl_2F]^+$ 616.2145; found 616.2148.

Separate the product of Example 7c into its enantiomers by chiral preparative HPLC using a Chiralpak AS column, eluting with 80:20 to 75:25 hexane:i-propylalcohol. The second enantiomer to eluting has an optical rotation of $[\alpha]_D^{25}=+8.8°$ (c=4.4 g/l in $CH_3OH$)

EXAMPLE 7d

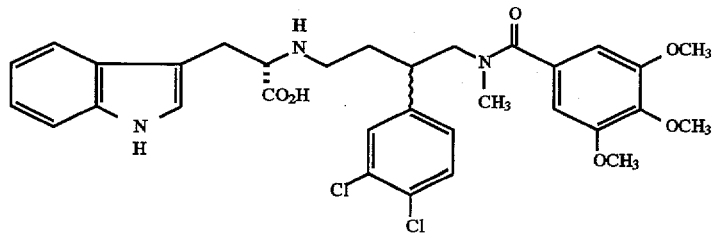

Using the procedure of Example 7, substitute L-tryptophan for Nω-methyltryptamine in step 2 to obtain the title compound. MS (FAB, M+H$^+$): m/e 628.

EXAMPLE 8

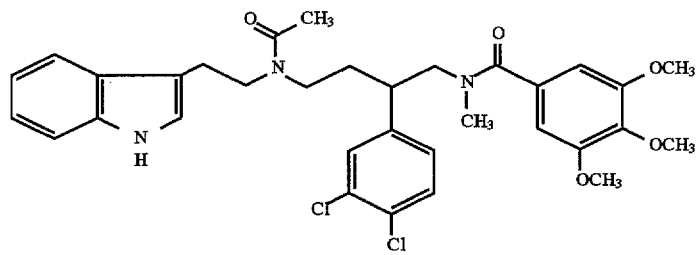

Treat a solution of the product from Example 7 (144.8 mg, 0.248 mmol) and pyridine (30 μL, 0.37 mmol) in $CH_2Cl_2$ (1.5 mL) with acetic anhydride (23.5 μL, 0.25 mmol) and stir for 35 min. Add the reaction mixture to 0.2N HCl (25 mL) and extract with $CH_2Cl_2$ (3×10 mL). Wash the combined organic layers with sat. $NaHCO_3$ (10 mL) and brine (10 mL), dry with $MgSO_4$, and concentrate. Chromatograph on silica gel, eluting with 20:1 $CH_2Cl_2$:$CH_3OH$, to obtain 127 mg of the desired product as a white foam (0.2 mmol, 82%). HRMS (FAB, M+H$^+$): m/e calc'd for $[C_{33}H_{38}N_3O_5Cl_2]^+$ 626.2189; found 626.2181.

EXAMPLE 9

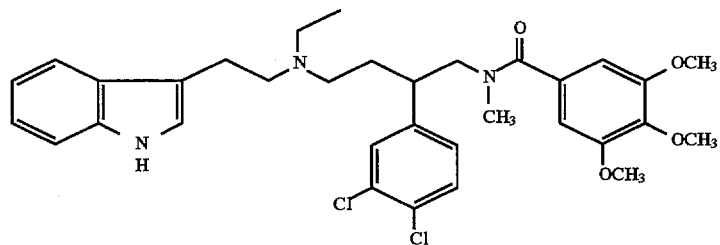

Treat a solution of the product from Example 7 (63.5 mg, 0.109 mmol) and $CH_3CH_2I$ (10 μL, 0.13 mmol) in DMF (1.1 mL) with 50% KF-celite (40.7 mg) and stir at 60° C. overnight. Add the reaction mixture to $H_2O$ (50 mL) and extract with EtOAc (3×25 mL). Wash the combined organic layers with brine (25 mL), dry with $MgSO_4$, and concentrate. Chromatograph on silica gel, eluting with 10:1 $CH_2Cl_2$:$CH_3OH$:$NH_3$ (aq), to obtain 42.7 mg of the product as a white foam (0.07 mmol, 64%). HRMS (FAB, M+H$^+$): m/e calc'd for $[C_{33}H_{40}N_3O_4Cl_2]^+$ 612.2396; found 612.2405.

Using the procedure of Example 9, substitute allyl bromide for $CH_3CH_2I$ to obtain the title compound. HRMS (FAB, M+H$^+$): m/e calc'd for $[C_{34}H_{40}N_3O_4Cl_2]^+$ 624.2396; found 624.2385.

EXAMPLE 9b

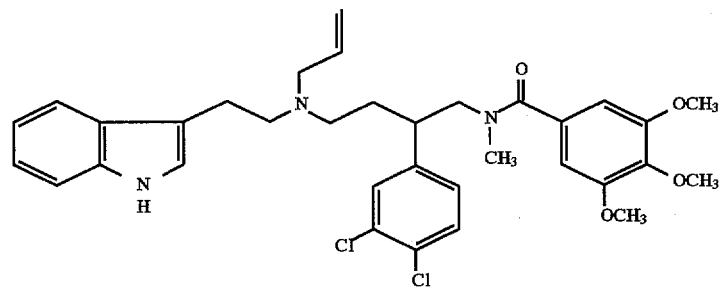

EXAMPLE 9c

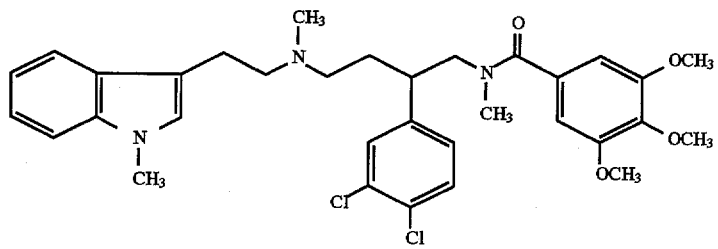

Use a procedure similar to Example 9, substituting $CH_3I$ (2 equivalents) for the alkylating agent and NaH for the base to obtain the title compound. HRMS (FAB, M+H$^+$): m/e calc'd for $[C_{33}H_{40}N_3O_4Cl_2]^+$ 612.2396; found 612.2407.

The following compound is isolated as a side product from the previous reaction:

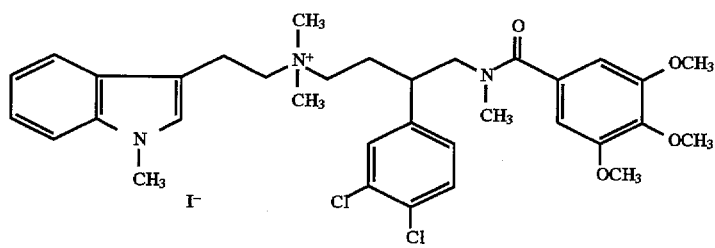

HRMS (FAB, M): m/e calc'd for $[C_{34}H_{42}N_3O_4Cl_2]^+$ 626.2552; found 15 626.2564.

EXAMPLE 10

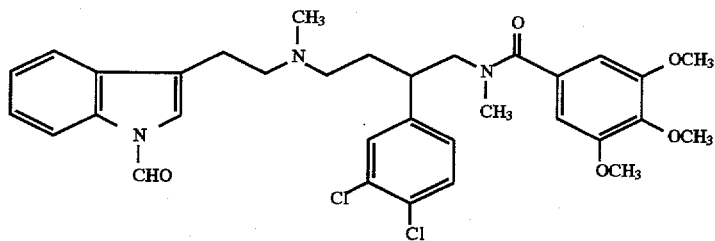

Treat the product of Example 2 (49.3 mg, 82 μmol) with formic acid (750 μL, 20 mmol) and acetic anhydride (30 mL, 0.32 mmol) and heat at 70° C. for 3 days. Add the reaction mixture to $H_2O$ (50 mL) and extract with $CH_2Cl_2$ (2×35 mL). Wash the combined organic layers with brine (25 mL), dry with $MgSO_4$ and concentrate. Chromatograph on silica gel, eluting with 20:1 to 10:1 $CH_2Cl_2$:$CH_3OH$:$NH_3$ (aq), to obtain 9.3 mg of the desired product as a white foam. HRMS (FAB, M+H$^+$): m/e calc'd for $[C_{33}H_{38}N_3O_5Cl_2]^+$ 626.2187; found 626.2189.

EXAMPLE 11

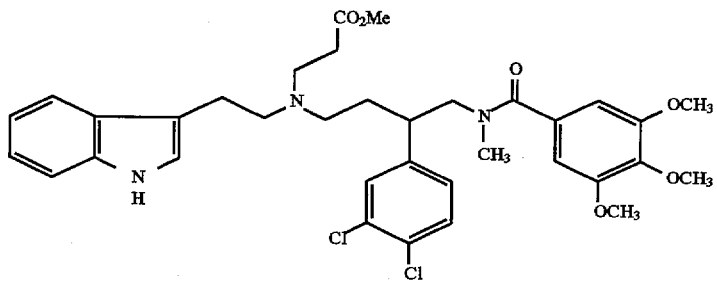

Step 1:

Treat a solution of the product of Example 7 (115.1 mg, 0.197 mmol) in DMF (2.0 mL) with methyl acrylate (30 μL, 0.33 mmol) and stir at 60° C. overnight. Add additional methyl acrylate (20 μL, 0.22 mmol) to the reaction mixture and stir at 60° C. for 24 h. Add the reaction mixture to H$_2$O (50 mL) and extract with EtOAc (3×25 mL). Wash the combined organic layers with brine (25 mL), dry with MgSO$_4$, and concentrate. Chromatograph on silica gel, eluting with 25:1 CH$_2$Cl$_2$:CH$_3$OH, to obtain 66.9 mg of the desired product (0.10 mmol, 51%). HRMS (FAB, M+H$^+$): m/e calc'd for [C$_{35}$H$_{42}$N$_3$O$_6$Cl$_2$]$^+$ 670.2451; found 670.2447.

EXAMPLE 12

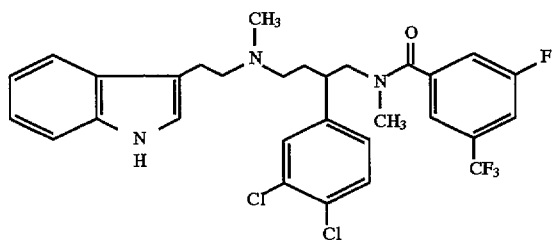

Step 1:

Heat a solution of the product of Example 1, step 4 (5.8 g, 17 mmol) in ethyl formate (100 mL) at reflux for 65 h and concentrate. Chromatograph on silica gel, eluting with 1:1 hexane:EtOAc, to obtain 4.4 g of the desired formamide as a colorless oil (12 mmol, 72%).

Step 2:

Treat a solution of the product of step 1 (4.2 g, 11.6 mmol) in Et$_2$O (25 mL) with BH$_3$.DMS (7.5 mL, 75 mmol) and stir at ambient temperature for 24 h. After concentrating the reaction mixture, quench the excess BH$_3$.DMS by the careful addition of CH$_3$OH. Add HCl-saturated CH$_3$OH to the resulting mixture, heat at 60° C. for 1 h and concentrate to give 3.08 g of N-methyl-4-amino-3-(3,4-dichlorophenyl)-butanol.

Step 3:

Treat the crude product of step 2 (3.08 g) with K$_2$CO$_3$ (3.02 g) and (BOC)$_2$O (3.43 g, 15.7 mmol) in CH$_3$OH (30 mL) for 2.5 h, filter and concentrate. Chromatograph on silica gel, eluting with 1:1 hexane:EtOAc, to obtain 2.50 g of the BOC-protected product (7.2 mmol, 62% for 2 steps).

Step 4:

To a −55° C. solution of oxalyl chloride (0.94 mL, 10.8 mmol) in CH$_2$Cl$_2$ (20 mL), slowly add DMSO (1.0 mL, 14.1 mmol) followed by a solution of the alcohol from step 3 (2.50 g, 7.2 mmol) in CH$_2$Cl$_2$ (35 mL). After stirring for 30 min. at −55° C., add Et$_3$N (4.0 mL, 29 mmol) and stir for 2 h at −55° C. Add 20% sat. KHSO$_4$ (28 mL) and Et$_2$O (35 mL), warm to room temperature and stir for 30 min. Add to Et$_2$O (100 mL), remove the aqueous layer, wash with sat. NaHCO$_3$ (3×35 mL), H$_2$O (35 mL) and brine (35 m). Dry the solution with MgSO$_4$ and concentrate to give 2.5 g of desired aldehyde product (quantitative yield).

Step 5:

Treat a solution of the product of step 4 (2.50 g, 7.2 mmol), N-methyl tryptamine (13.8 mmol) and crushed 3A mol. sieves (2.0 g) in CF$_3$CH$_2$OH (25 mL) with NaCNBH$_3$ (1.75 g, 27.8 mmol). Stir for 1 h, add H$_2$O (250 mL) and extract with 2:1 CH$_2$Cl$_2$:Et$_2$O (3×150 mL). Wash the combined organic layers with brine (150 mL), dry with MgSO$_4$ and concentrate. Chromatograph the crude product on silica gel, eluting with 10:1:0.1 CH$_2$Cl$_2$:CH$_3$OH:NH$_3$ (aq.) to give 2.5 g of product as a white foam (5.0 mmol, 69%).

Step 6:

Treat the product of step 5 (4.5 g, 8.9 mmol) with trifluoroacetic acid (30 mL) for 2 h and concentrate. Suspend the residue in saturated NaHCO$_3$ and extract with CH$_2$Cl$_2$. Wash the combined organic layers with brine, dry with MgSO$_4$ and concentrate. Chromatograph on silica gel, eluting with 10 to 20% NH$_3$ saturated CH$_3$OH:CH$_2$Cl$_2$, to obtain 2.0 g of the amino product as a white solid (4.9 mmol, 55%).

Step 7:

Convert the product from step 6 to the title compound using a procedure similar to that described in Example 2, Step 1, substituting 3,4,5-trimethoxybenzoic acid for 3-fluoro-5-trifluromethylbenzoic acid. HRMS (FAB, M+H$^+$): m/e calc'd for [C$_{30}$H$_{30}$N$_3$OCl$_2$F$_4$]$^+$ 594.1702; found 594.1702.

Using the procedure of Example 12, substitute the appropriate acid in step 7 to obtain the compounds of the following structure, wherein W is as shown in the table:

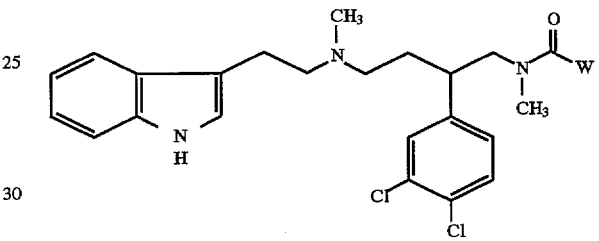

| Ex. | W | HRMS (FAB, M + H$^+$): m/e calc'd | HRMS (FAB, M + H$^+$): m/e found |
|---|---|---|---|
| 12a | ![benzodioxole] | 552.1821 | 552.1816 |
| 12c | ![3-chloro-5-methylpyridyl] | 557.1642 | 557.1644 |
| 12d | ![4-methoxycyclohexyl] | 544.2498 | 544.2499 |
| 12e | ![3-CF$_3$-phenyl] | 576.1796 | 576.1796 |
| 12f | ![4-CF$_3$-phenyl] | 576.1796 | 576.1792 |
| 12g | ![4-OCF$_3$-phenyl] | 592.1745 | 592.1746 |

-continued

| Ex. | W | HRMS (FAB, M + H⁺): m/e calc'd | HRMS (FAB, M + H⁺): m/e found |
|---|---|---|---|
| 12h | pyridine with Cl, Cl substituents | 577.1095 | 577.1087 |
| 12i | 2,4-dichlorophenyl | | MS (FAB, M + H⁺): m/e 576 |
| 12j | 3,5-dimethylphenyl | 536.2235 | 536.2249 |
| 12k | 3-NO₂-5-CF₃-phenyl | 621.1647 | 621.1646 |
| 12l | 2,6-dimethyl-4-OCH₃-phenyl | 566.2341 | 566.2345 |

EXAMPLE 13

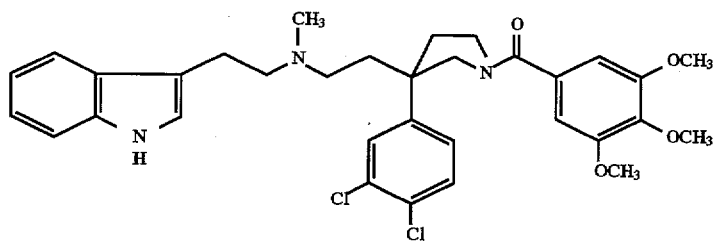

Treat 3,4-dichloro-beta-(2-oxoethyl)-N-methyl-N-phenylbenzenepropanamide (0.53 g) in $CH_3OH$ (35 mL) sequentially with molecular sieves 3A (5.5 g), isoquinoline HCl (0.33 g) and $NaBH_3CN$ (0.4 g). Stir the resulting mixture at room temperature for 20 hours, filter through a pad of celite and concentrate under reduced pressure. Partition the residue between 10% $NH_4OH$ solution and $CH_2Cl_2$ (25 mL), separate the organic layer and extract the aqueous layer with $CH_2Cl_2$ (2×25 mL). Dry the combined organic layers over $MgSO_4$, filter and concentrate under reduced pressure to give a crude oil (0.7 g). Chromatograph on silica gel, eluting with 2% $CH_3OH/CH_2Cl_2$ to obtain the title compound (0.27 g). Mass spectrum (FAB): 467.

EXAMPLE 14

Use 3-(3,4-dichlorophenyl)-3-(2-hydroxyethyl)-pyrrolidine in the procedure of Example 12, steps 3–7, substituting 3,4,5-trimethoxybenzoic acid for 3-fluoro-5-trimethylbenzoic acid to obtain the title compound. HRMS (FAB, M+H⁺): m/e calc'd for $[C_{33}H_{37}N_3O_4Cl_2]^+$ 610.2239; found 610.2219.

EXAMPLE 14a

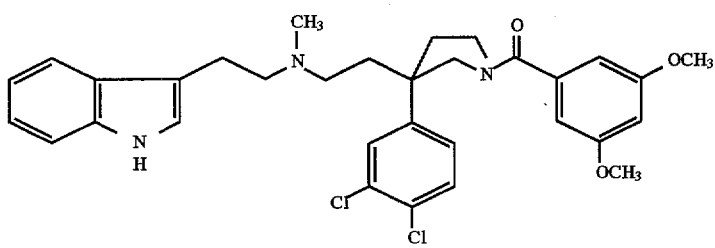

Use the procedure of Example 14, substituting 3,5-dimethoxy-benzoic acid for 3,4,5-trimethoxybenzoic acid to obtain the title compound. HRMS (FAB, M+H$^+$): m/e calc'd for [$C_{32}H_{36}N_3O_3Cl_2$]$^{1+}$ 580.2134; found 580.2116.

EXAMPLE 14b

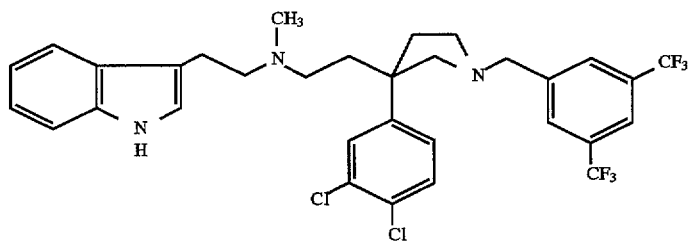

Using the procedure of Example 14, substitute 3,5-bis(trifluoromethyl)benzoic acid for 3,4,5-trimethoxybenzoic acid to obtain the title compound. HRMS (FAB, M+H$^+$): m/e calc'd for [$C_{32}H_{30}N_3OCl_2F_6$]$^{1+}$ 656.1670; found 656.1663.

The following formulations exemplify some of the dosage forms of this invention. In each, the term "active compound" refers to a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
|   | Total | 300 | 700 |

Method of Manufacture

Mix Item Nos. 1 and 2 in suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Magnesium Stearate NF | 4 | 70 |
|   | Corn Starch, Food Grade | 40 | 7 |
|   | Total | 250 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

EXAMPLE C

Sterile Powder for Injection

| Ingredient | mg/vial | mg/vial |
|---|---|---|
| Active sterile powder | 100 | 500 |

For reconstitution add sterile water for injection or bacteriostatic water for injection.

The in vitro and in vivo activity of the compounds of formula I can be determined by the following procedures.

In Vitro Procedure to Identify NK$_1$ Activity

Test compounds are evaluated for their ability to inhibit the activity of the NK$_1$ agonist Substance P on the isolated guinea pig vas deferens. Freshly cut vas deferens are removed from male Hartley guinea pigs (230–350 g) and suspended in 25 ml tissue baths containing Kreb's Henseleit solution warmed to 37° C. and constantly aerated with 95% $O_2$ and 5% $CO_2$. Tissues are adjusted to 0.5 g and allowed to equilibrate for a period of 30 minutes. The vas deferens are exposed to an electrical field stimulation (Grass S48 Stimulator) every 60 seconds at an intensity that will cause the tissue to contract 80% of its maximum capacity. All responses are recorded isometrically by means of a Grass force displacement transducer (FT03) and Harvard electronic recorder. Substance P inhibits the electrical field stimulated-induced contractions of the guinea pig vas deferens. In unpaired studies, all tissues (control or drug treated) are exposed to cumulative concentrations of Substance P ($1\times10^{-10}$M–$7\times10^{-7}$M). Single log-concentrations of the test compounds are given to separate tissues and allowed to equilibrate for 30 minutes before a Substance P concentation-response curve is generated. At least 5 separate tissues are used for each control and individual drug-concentation for every drug assay.

Inhibition of the Substance P is demonstrated by a rightward shift of its concentration-response curve. These shifts are used to determine the $pA_2$ value, which is defined as the negative log of the molar concentration of the inhibitor which would require that twice as much agonist be used to elicit a chosen response. This value is used to determine relative antagonist potency.

Isolated Hamster Trachea $NK_2$ Assay

General methodology and characterization of hamster trachea responses to neurokinin agonists as providing an $NK_2$ monoreceptor assay is found in C. A. Maggi, et al., *Eur. J. Pharmacol.* 166 (1989) 435 and J. L. Ellis, et al., *J. Pharm. Exp. Ther.* 267 (1993) 95.

Continuous isometric tension monitoring is achieved with Grass FT-03 force displacement transducers connected to Buxco Electronics preamplifiers built into a Graphtec Linearcorder Model WR 3310.

Male Charles River LAK:LVG (SYR) hamsters, 100–200 g fed weight, are stunned by a sharp blow to the head, loss of corneal reflex is assured, the hamsters are sacrificed by thoracotomy and cutting the heart. Cervical trachea segments are removed to room temperature Krebs buffer, pH 7.4, aerated with 95% $O_2$-5% $CO_2$ gas and cleaned of adhering tissue. The segments are cut into two 3–4 mm long ring segments. Tracheal rings are suspended from transducers and anchored in 15.0 ml water jacketed organ baths by means of stainless steel hooks and 6-0 silk. Baths are filled with Krebs buffer, pH 7.4, maintained at 37° C. and continuously aerated with 95% $O_2$-5% $CO_2$ gas. Tracheal rings are placed under 1.0 g initial tension and allowed a 90 min equilibration period with four 1 µM NKA challenge, wash and recovery cycles at 20 min intervals. 30 min vehicle pretreatment is followed by cumulative additions of rising doses of NKA (3 nM–1 µM final concentration, 5 min intervals between additions). The final NKA response is followed by a 15 min wash and recovery period. 30 min pretreatment with a test compound or its vehicle is followed by cumulative additions of rising doses of NKA (3 nM–10 µM final concentration if necessary, 5 min intervals between additions). The final NKA response is followed by a 1 mM carbachol challenge to obtain a maximal tension response in each tissue.

Tissue responses to NKA are recorded as positive pen displacements over baseline and converted to grams tension by comparison to standard weights. Responses are normalized as a % of the maximal tissue tension. $ED_{50}$'s are calculated for NKA from the control and treated NKA dose responses and compared. Test compounds resulting in an agonist dose ratio $\geq 2$ at a screening concentration of 1 µM (i.e. $pA_2 \geq =6.0$) are considered actives. Further dose response data is obtained for actives so that an apparent $pA_2$ estimate can be calculated. $pA_2$ is calculated either by estimation of $K_i$ as described by Furchgott (where $pA_2$=−Log $K_i$, R. F. Furchgott, *Pharm. Rev.* 7 [1995] 183) or by Shild Plot Analysis (O. Arunlakshana & H. O. Shild, *Br. J. Pharmacol.* 14]1959] 48) if the data is sufficient.

Effect of $NK_1$ Antagonists on Substance P-induced Airway Microvascular Leakage in Guinea Pigs Studies are performed on male Hartley guinea pigs ranging in weight from 400–650 g. The animals are given food and water ad libitum. The animals are anesthetized by intraperitoneal injection of dialurethane (containing 0.1 g/ml diallylbarbituric acid, 0.4 g/ml ethylurea and 0.4 g/ml urethane). The trachea is cannulated just below the larynx and the animals are ventilated ($V_T$=4 ml, f=45 breaths/min) with a Harvard rodent respirator. The jugular vein is cannulated for the injection of drugs.

The Evans blue dye technique (Danko, G. et al., *Pharmacol. Commun.*, 1, 203–209, 1992) is used to measure airway microvascular leakage (AML). Evans blue (30 mg/kg) is injected intravenously, followed 1 min later by i.v. injection of substance P (10 µg/kg). Five min later, the thorax is opended and a blunt-ended 13-guage needle passed into the aorta. An incision is made in the right atrium and blood is expelled by flushing 100 ml of saline through the aortic catheter. The lungs and trachea are removed en-bloc and the trachea and bronchi are then blotted dry with filter paper and weighed. Evans blue is extracted by incubation of the tissue at 37° C. for 18 hr in 2 ml of formamide in stoppered tubes. The absorbance of the formamide extracts of dye is measured at 620 nm. The amount of dye is calculated by interpolation from a standard curve of Evans blue in the range 0.5–10 µg/ml in formamide. The dye concentration is expressed as ng dye per mg tissue wet weight. Test compounds were suspended in cyclodextran vehicle and given i.v. 5 min before substance P.

Measurement of $NK_2$ Activity In Vivo

Male Hartley guinea pigs (400–500 gm) with ad lib. access to food and water are anesthetized with an intraperitoneal injection of 0.9 ml/kg dialurethane (containing 0.1 g/m diallylbarbituric acid, 0.4 g/ml ethylurea and 0.4 g/ml urethane). After induction of a surgical plane of anesthesia, tracheal, esophageal and jugular venous cannulae are implanted to facilitate mechanical respiration, measurement of esophageal pressure and administration of drugs, respectively.

The guinea pigs are placed inside a whole body plethysmograph and the catheters connected to outlet ports in the plethysmograph wall. Airflow is measured using a differential pressure transducer (Validyne, Northridge Calif., model MP45-1, range±2 $cmH_2O$) which measures the pressure across a wire mesh screen that covers a 1 inch hole in the wall of the plethysmograph. The airflow signal is electrically integrated to a signal proportional to volume. Transpulmonary pressure is measured as the pressure difference between the trachea and the esophagus using a differential pressure transducer (Validyne, Northridge, Calif., model MP45-1, range±20 cm $H_2O$). The volume, airflow and transpulmonary pressure signals are monitored by means of a pulmonary analysis computer (Buxco Electronics, Sharon, Conn., model 6) and used for the derivation of pulmonary resistance ($R_L$) and dynamic lung compliance ($C_{Dyn}$).

Bronchoconstriction Due to NKA

Increasing iv doses of NKA are administered at half log (0.01–3 μg/kg) intervals allowing recovery to baseline pulmonary mechanics between each dose. Peak bronchoconstriction occurs within 30 seconds after each dose of agonist. The dose response is stopped when $C_{Dyn}$ is reduced 80–90% from baseline. One dose-response to NKA is performed in each animal. Test compounds are suspended in cyclodextran vehicle and given i.v. 5 min before the initiation of the NKA dose response.

For each animal, dose response curves to NKA are constructed by plotting the percent increase in $R_L$ or decrease in $C_{Dyn}$ against log dose of agonist. The doses of NKA that increased $R_L$ by 100% ($R_L100$) or decreased $C_{Dyn}$ by 40% ($C_{Dyn}40$) from baseline values are obtained by log-linear interpolation of the dose response curves.

Neurokinin Receptor Binding Assay(s)

Chinese Hamster ovary (CHO) cells transfected with the coding regions for the human neurokinin 1 ($NK_1$) of the human neurokinin 2 ($NK_2$) receptors are grown in Dulbecco's minimal essential medium supplemented with 10% fetal calf serum, 0.1 mM non-essential amino acids, 2 mM glutamine, 100 units/ml of penicillin and streptomycin, and 0.8 mg of G418/ml at 37° C. in a humidified atmosphere containing 5% $CO_2$.

Cells are detached from T-175 flasks with a sterile solution containing 5 mM EDTA in phosphate buffered saline. Cells are harvested by centrifugation and washed in RPMI media at 40° C. for 5 minutes. The pellet is resuspended in Tris-HCl (pH7.4) containing 1 μM phsphoramidon and 4 ug/ml of chymostatin at a cell density of $30\times10^6$ cells/ml. The suspension is then homogenized in a Brinkman Polytron (setting 5) for 30–45 seconds. The homogenate is centrifuged at 800×g for 5 min at 4° C. to collect unbroken cells and nuclei. The supernatant is centrifuged in a Sorvall RC5C at 19,000 rpm (44,00×g) for 30 min at 4° C. The pellet is resuspended, an aliquot is removed for a protein determination (BCA) and washed again. The resulting pellet is stored at −80° C.

To assay receptor binding, 50 μl of [$^3$H]-Substance P (9-Sar, 11-Met [02]) (specific activity 41 Ci/mmol) (Dupont-NEN) (0.8 nM for the NK-1 assay) or [$^3$H]-Neurokinin A (specific activity 114 Ci/mmole) (Zenca) (1.0 nM for the NK-2 assay) is added to tubes containing buffer (50 mM Tris-HCl (pH 7.4) with 1 mM $MnCl_2$ and 0.2% Bovine Serum Albumin) and either DMSO or test compound. Binding is initiated by the addition of 100 μl of membrane (10–20 μg) containing the human NK-1 or NK-2 receptor in a final volume of 200 μl. After 40 minutes at room temperature, the reaction is stopped by rapid filtration onto Whatman GF/C filters which have been presoaked in 0.3% polyethyleneimine. Filters are washed 2 times with 3 ml of 50 mM Tris-HCl (pH$_{7.4}$). Filters are added to 6 mls of Ready-Safe liquid scintillation cocktail and quantified by liquid scintillation spectrometry in a LKB 1219 RackBeta counter. Non-specific binding is determined by the addition of either 1 μM of CP-99994 (NK-1) or 1 μM SR-48968 (NK-2) (both synthesized by the chemistry department of Schering-Plough Research Institute). $IC_{50}$ values are determined from competition binding curves and Ki values are determined according to Cheng and Prusoff using the experimentally determined value of 0.8 nM for the NK-1 receptor and 2.4 nM for the NK-2 receptor.

$NK_3$ activity is determined by following a procedure similar to that described in the literature, e.g., *Molecular Pharmacol.*, 48 (1995), p. 711–716.

% Inhibition is the difference between the percent of maximum specific binding (MSB) and 100%. The percent of MSB is defined by the following equation, wherein "dpm" is disintegrations per minute:

$$\% MSB = \frac{(dpm \text{ of unknown}) - (dpm \text{ of nonspecific binding})}{(dpm \text{ of total binding}) - (dpm \text{ of nonspecific binding})} \times 100$$

It will be recognized that compounds of formula I exhibit $NK_1$, $NK_2$ and/or $NK_3$ antagonist activity to varying degrees, e.g., certain compounds have strong $NK_1$ antagonist activity, but weaker $NK_2$ and $NK_3$ antagonist activity, while others are strong $NK_2$ antagonists, but weaker $NK_1$ and $NK_3$ antagonists. While compounds with approximate equipotency are preferred, it is also within the scope of this invention to use compounds of with unequal $NK_1/NK_2/NK_3$ antagonist activity when clinically appropriate.

Using test procedures described above, the following data (% inhibition or Ki) were obtained for preferred and/or representative compounds of formula I:

| Ex. | % Inhibition $NK_1$ (1 μM dose) | Ki ($NK_1$) (nM) | % Inhibition $NK_2$ (1 μM dose) | Ki ($NK_2$) (nM) | Ki ($NK_3$) (nM) |
|---|---|---|---|---|---|
| 7b | — | 19 | — | 217 | — |
| 14b | 81 | 21 | 88 | 143 | — |
| 12c | 82 | 103 | 93 | 39 | — |
| 7d | — | 233 | — | 30 | — |
| 2 | 81 | 25 | 87 | 33 | 448 |
| 7c | — | 12 | 100 | 10 | — |

Compounds of the present invention exhibit a range of activity: percent inhibition at a dosage of 1 μM ranges from about 0 to about 100% inhibition of $NK_1$ and/or about 0 to about 100% inhibition of $NK_2$. Preferred are compounds having a Ki≦100 nM for the $NK_1$ receptor. Also preferred are compounds having a Ki≦100 nM for the $NK_2$ receptor. Another group of preferred compounds are those having a Ki≦100 nM for each of the $NK_1$ and $NK_2$ receptors.

We claim:

1. A compound represented by the structural formula

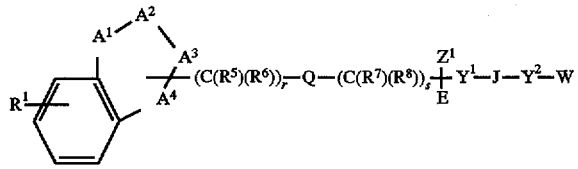

or a pharmaceutically acceptable salt thereof, wherein:

$A^1$, $A^2$, $A^3$ and $A^4$ are independently selected from the group consisting of —(C($R^2$)($R^{10}$))—, —(C($R^{2c}$)($R^{10}$))—, —(C($R^2$))=, —(C($R^{2c}$))=, —$NR^{16}$—, —N=, —O—, —S(O)$_e$—, —C(O)— and a bond, wherein $A^1$, $A^2$, $A^3$ and $A^4$, together with the carbon atoms to which they are attached, form a 5- or 6-membered ring, and wherein two adjacent A groups are selected from the group consisting of the following combinations:

—(C($R^2$)($R^{10}$))—(C($R^2$)($R^{10}$))—;
—(C($R^2$)($R^{10}$))—(C($R^{2c}$))=;
—(C($R^{2c}$)($R^{10}$))—$NR^{16}$—;
—(C($R^{2c}$)($R^{10}$))—N=;
—(C($R^{2c}$)($R^{10}$))—O—;
—(C($R^{2c}$)($R^{10}$))—S(O)$_e$—;
—(C($R^2$)($R^{10}$)—C(O)—;
—(C($R^2$))=(C($R^2$))—;

—(C(R²))═N—;
═(C(R²))—(C(R²))═;
═(C(R²))—NR¹⁶—;
═(C(R²))—N═;
═(C(R²))—O—;
═(C(R²))—S(O)$_e$—;
═(C(R²))—C(O)—;
—NR¹⁶—N═;
—NR¹⁶—S(O)$_e$—;
—NR¹⁶—C(O)—;
—N═N—;
═N—N═;
═N—O—;
═N—S(O)$_e$—;
═N—C(O)—;
—O—S(O)$_e$—; and
—O—C(O)—;

provided that three adjacent A groups do not represent —C(O)—O—C(O)—, —S(O)—O—C(O)— or —S(O)—O—S(O)—, and provided that when an aromatic nitrogen is present in the ring formed by A¹, A², A³ and A⁴, the N-oxide can be formed;

E is R³-aryl or R³-heteroaryl;

W is R⁴-cycloalkyl, R⁴-aryl, R⁴-heterocycloalkyl or R⁴-heteroaryl;

R¹, R³ and R⁴ are independently 1–3 substituents independently selected from the group consisting of H, halogeno, $C_1$–$C_6$ alkyl, —CF₃, —C₂F₅, —OR¹¹, —COR¹¹, —CO₂R¹¹, —CON(R¹¹)(R¹²), —N(R¹¹)(R¹²), —N(R¹¹)COR¹², —SH, —S(O)$_e$R¹³, —OC(O)R¹¹, —OC(O)N(R¹¹)(R¹²), —NR¹¹CO₂R¹³, —NR¹¹C(O)N(R¹²)(R¹⁴), R¹⁵-phenyl, R¹⁵-benzyl, —NO₂, —NR¹¹S(O)₂R¹³ and —S(O)₂NR¹¹R¹²; or adjacent R¹, R³ or R⁴ substituents can form a —O—CH₂—O— group;

R² is independently selected from the group consisting of R²ᵃ, R²ᵇ or R¹⁰; and R²ᶜ is independently selected from the group consisting of R²ᵃ and R¹⁰; wherein R²ᵃ is selected from the group consisting of —CF₃, —C₂F₅, —COR¹¹, —CO₂R¹¹, —CON(R¹¹)(R¹²), R¹⁵-phenyl and R¹⁵-benzyl; and R²ᵇ is selected from the group consisting of halogeno, —OR¹¹, —NO₂, —N(R¹¹)(R¹²), —N(R¹¹)COR¹², —SH, —S(O)$_e$R¹³, —OC(O)R¹¹, —OC(O)N(R¹¹)(R¹²), —NR¹¹CO₂R¹³, —NR¹¹C(O)N(R¹²)(R¹⁴), —NR¹¹S(O)₂R¹³ and —S(O)₂NR¹¹R¹²; provided that from any combination of ring members A¹, A², A³ and A⁴ comprising R² and R²ᶜ, no more than one substituent can be selected from R²ᵃ and no more than one substituent can be selected from R²ᵇ;

R⁵, R⁷, R⁹, R¹¹, R¹² and R¹⁴ are independently selected from the group consisting of H, $C_1$–$C_6$ alkyl, R¹⁵-phenyl, R¹⁵-benzyl, —CF₃ and —C₂F₅;

R⁶ and R⁸ are independently selected from the group consisting of R⁵, —(C(R⁹)(R¹⁰))$_n$—OR¹¹, —(C(R⁹)(R¹⁰))$_n$—NR¹¹R¹², —(C(R⁹)(R¹⁰))$_n$—SH, —(C(R⁹)(R¹⁰))$_n$—S(O)$_e$R¹³, —(C(R⁹)(R¹⁰))$_n$—CO₂R¹¹, —(C(R⁹)(R¹⁰))$_n$—OC(O)R¹¹, —(C(R⁹)(R¹⁰))$_n$—CONR¹¹R¹², —(C(R⁹)(R¹⁰))$_n$—COR¹¹ and —(C(R⁹)(R¹⁰))$_n$—NR¹¹C(O)R¹², provided that when Q is a heteroatom, R⁶ and R⁸ cannot be —OR¹¹, —OC(O)R¹¹, —N(R¹¹)COR¹², —NR¹¹R¹², —SH or —S(O)$_e$R¹³ on adjacent carbon atoms;

R¹⁰ is independently selected from the group consisting of hydrogen and $C_1$–$C_6$ alkyl;

R¹³ is independently selected form the group consisting of $C_1$–$C_6$ alkyl, R¹⁵-phenyl, R¹⁵-benzyl, —CF₃ and —C₂F₅;

R¹⁵ is hydrogen, $C_1$–$C_6$ alkyl, $C_1$–$C_6$ alkoxy or halogeno;

Q is a bond, —C(O)—, —NR¹⁷—, —(C(R⁹)(R¹⁰))—, —O—, —S(O)$_e$—, —C(X)NR¹¹—, —N(R¹¹)C(X)—, —N(R¹¹)SO₂—, —SO₂N(R¹¹)— or —N⁺(R¹¹)(R¹⁷)—;

R¹⁶ and R¹⁷ are independently selected from the group consisting of hydrogen, $C_1$–$C_6$ alkyl, —S(O)$_e$R¹³, —COR¹¹, —(CH₂)$_m$—CO₂R¹³, —CONR¹¹R¹², $C_2$–$C_6$ alkenyl, —R¹⁵-phenyl and R¹⁵-benzyl;

X is ═O, ═S or ═N(R¹²);

Y¹ is —(C(R⁹)(R¹⁰))$_m$—, —G—(C(R⁹)(R¹⁰))$_m$— or —(C(R⁹)(R¹⁰))$_m$—G—;

G is

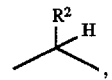

provided that when m is 0, R² is H, $C_1$–$C_6$ alkyl, —CF₃, —C₂F₅, —COR¹¹, —CO₂R¹¹, —CON(R¹¹)(R¹²), R¹⁵-phenyl or R¹⁵-benzyl;

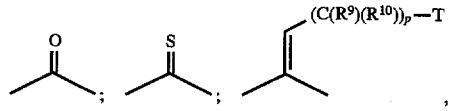

provided that when p is 0, T is not OH or —NR¹¹R¹²;

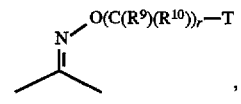

provided that when r is 1, T is not OR¹¹ or —NR¹¹R¹²; or

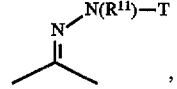

provided T is not —OR¹¹, —N(R¹¹)(R¹²), —S(O)$_e$R¹³, —NR¹¹CO₂R¹³, —NR¹¹COR¹², —NR¹¹CON(R¹²)(R¹⁴) or —OC(O)N(R¹¹)(R¹²);

T is H, R¹⁵-aryl, R¹⁵-heterocycloalkyl, R¹⁵-heteroaryl, R¹⁵-cycloalkyl, —OR¹¹, —N(R¹¹)(R¹²), —COR¹¹, —CO₂R¹¹, —CON(R¹¹)(R¹²), —S(O)$_e$R¹³, —NR¹¹CO₂R¹³, —NR¹¹COR¹², —NR¹¹CON(R¹²)(R¹⁴) or —OC(O)N(R¹¹)(R¹²);

J is a bond, —S(O)$_e$—, —O— or —N(Z²)—, —N(Z²)C(O)— or —N(Z²)C(S)—; and when G is —C(R²)H—, J can also be —N(Z²)C(O)O— or —OC(O)N(Z²)—;

Y² is —(C(R⁹)(R¹⁰))$_m$—;

Z¹ is H, $C_1$–$C_6$ alkyl, R¹⁵-phenyl, R¹⁵-benzyl, —CF₃, —C₂F₅, —NR¹¹R¹², —OR¹¹ or SR¹¹; Z² is H, $C_1$–$C_6$ alkyl, R¹⁵-phenyl, R¹⁵-benzyl, —CF₃ or —C₂F₅; provided that when Y¹ is —(C(R⁹)(R¹⁰))$_m$— and m is 0, Z¹ is not —NR¹¹R¹², —OR¹¹ or —SR¹¹; or Z¹ and Z² together are —(C(R⁹)(R¹⁰))$_u$—, wherein u is 1 to 4, and wherein with the atoms to which they are attached, form a 4 to 8 membered ring;

e and n are independently 0, 1 or 2;

m and p are independently 0, 1, 2 or 3; and r and s are independently 1, 2, 3 or 4.

2. A compound of claim 1 wherein $A^4$ is a bond.

3. A compound of claim 1 wherein E is $R^3$-phenyl.

4. A compound of claim 1 wherein $R^1$, $R^2$, $R^3$ and $R^4$ are independently selected from the group consisting of H, halogeno, $C_1$–$C_6$ alkyl, —$CF_3$, —$OR^{11}$, —$COR^{11}$, —$CO_2R^{11}$, —$CON(R^{11})(R^{12})$ and —$N(R^{11})(R^{12})$.

5. A compound of claim 1 wherein $R^5$, $R^7$, $R^9$, $R^{11}$, $R^{12}$ and $R^{14}$ are independently selected from the group consisting of H, $C_1$–$C_6$ alkyl and —$CF_3$.

6. A compound of claim 1 wherein $R^6$ and $R^8$ are independently selected from the group consisting of hydrogen, —$(C(R^9)(R^{10}))_n$—$OR^{11}$, —$(C(R^9)(R^{10}))_n$—$NR^{11}R^{12}$, —$(C(R^9)(R^{10}))_n$—$SR^{11}$, —$(C(R^9)(R^{10}))_n$—$CO_2R^{11}$, —$(C(R^9)(R^{10}))_n$—$CONR^{11}R^{12}$ and —$(C(R^9)(R^{10}))_n$—$COR^{11}$.

7. A compound of claim 6 wherein $R^6$ and $R^8$ are each hydrogen or $R^8$ is hydrogen and $R^6$ is —$(C(R^9)(R^{10}))_n$—$CO_2R^{11}$.

8. A compound of claim 1 wherein $Z^1$ is hydrogen or $Z^1$ and $Z^2$ together are ethylene or propylene, and with the atoms to which they are attached form a 5- or 6-membered ring.

9. A compound of claim 1 wherein Q is —$NR^{17}$—, —O— or —$S(O)_e$—.

10. A compound of claim 9 wherein Q is —$NR^{17}$—, wherein $R^{17}$ is hydrogen, $C_1$–$C_6$ alkyl or $C_2$–$C_6$ alkenyl.

11. A compound of claim 1 wherein $A^1$, $A^2$, $A^3$ and $A^4$, together with the benzene ring to which they are attached, comprise an indolyl ring.

12. A compound of claim 11 wherein $Y^1$ is —$(C(R^9)(R^{10}))_m$—, —G—$(C(R^9)(R^{10}))_m$— or $(C(R^9)(R^{10}))_m$—G—, wherein m is 0 or 1.

13. A compound of claim 11 wherein $Y^1$ is —$(C(R^9)(R^{10}))_m$— or —$(C(R^9)(R^{10}))_m$—G—, $Y^2$ is —$(C(R^9)(R^{10}))_m$— and m is zero or 1.

14. A compound of claim 13 wherein J is —O—, —$N(Z^2)$— or —$N(Z^2)C(O)$—.

15. A compound of claim 14 wherein $Z^1$ is hydrogen or $Z^1$ and $Z^2$ together are ethylene or propylene, and with the atoms to which they are attached form a 5- or 6-membered ring.

16. A compound of claim 15 wherein $R^5$, $R^6$, $R^7$ and $R^8$ are each hydrogen and Q is —$NR^{17}$—.

17. A compound of claim 16 wherein s is 2, J is —$N(Z^2)$C(O)—, and W is $R^4$-cycloalkyl, $R^4$-aryl or $R^4$-heteroaryl.

18. A compound of claim 1 selected from the group consisting of

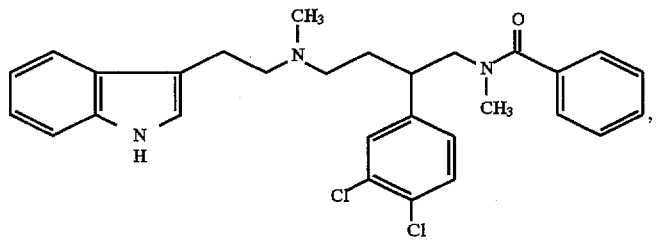

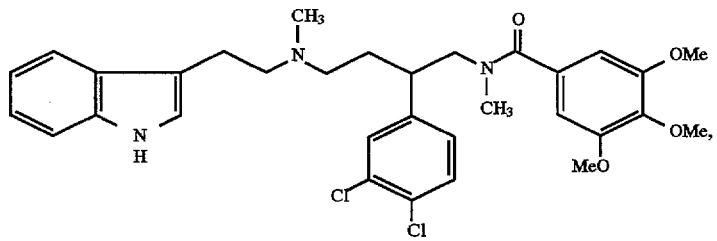

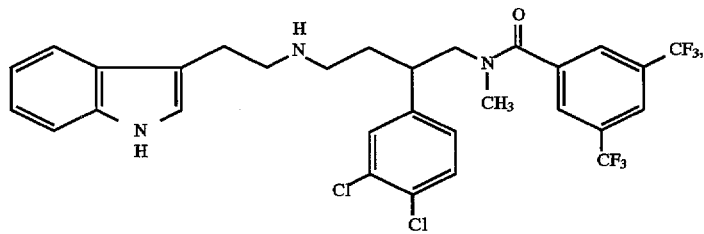

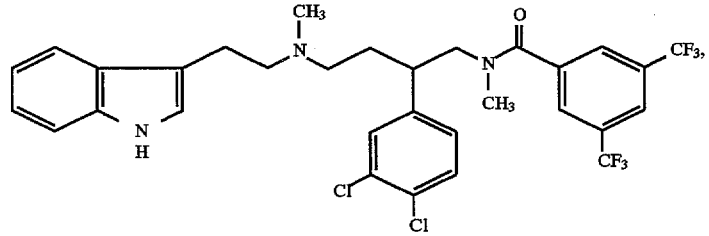

-continued
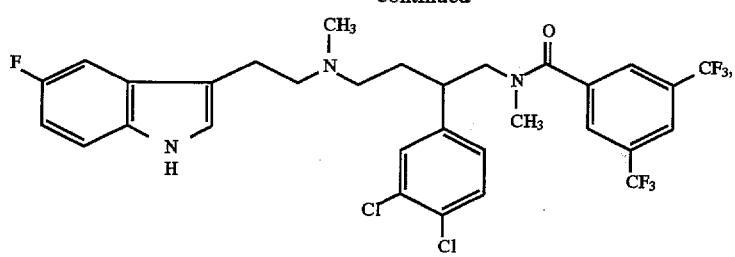
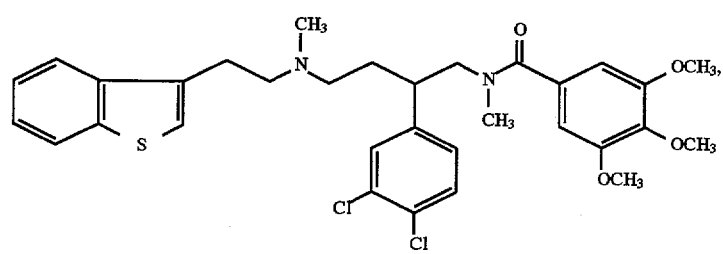
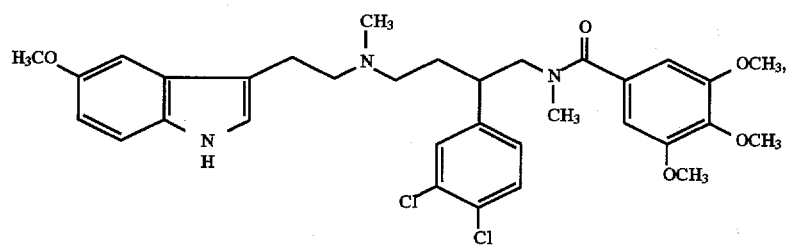
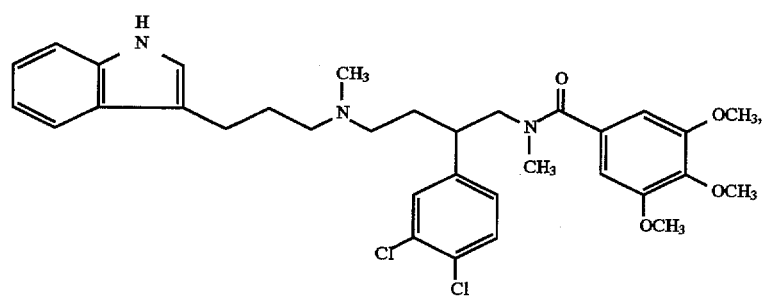
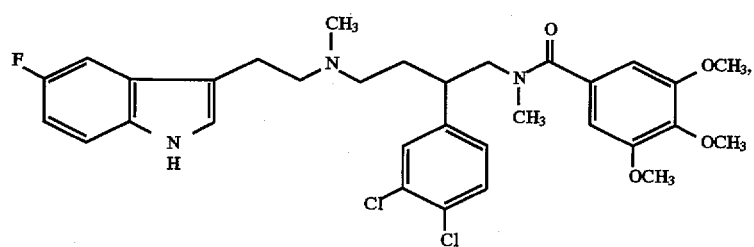
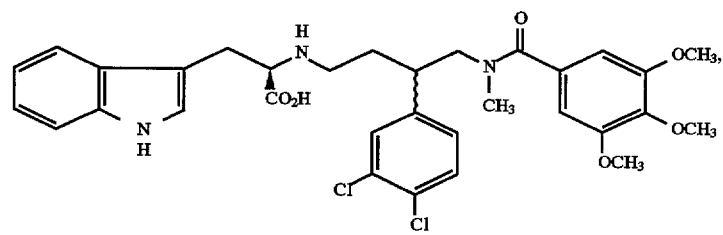

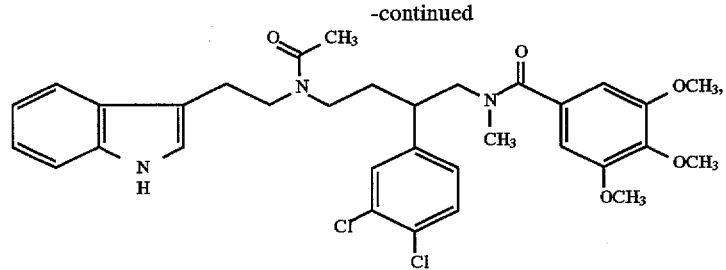
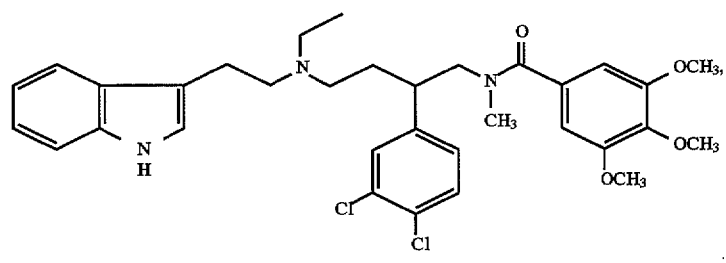
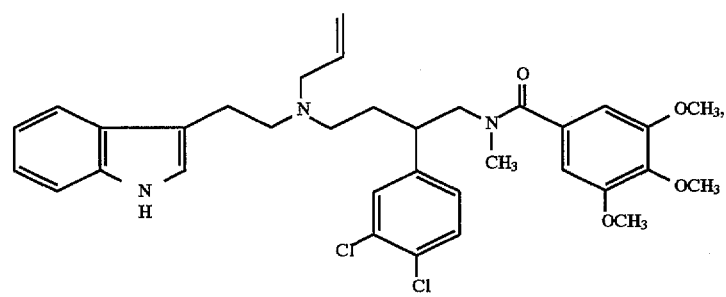
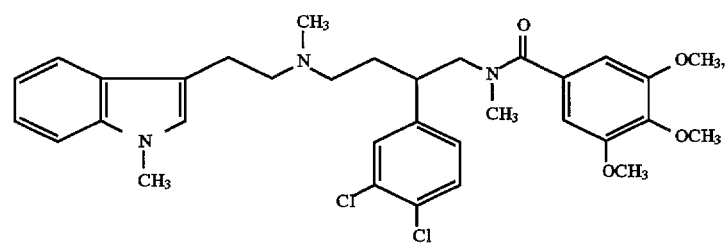
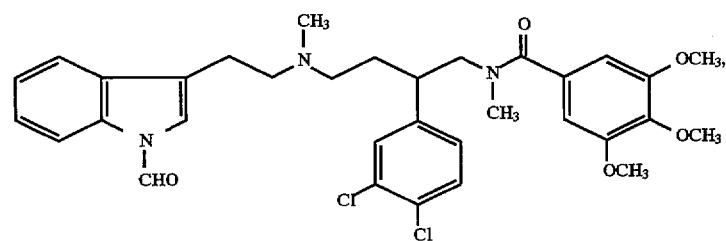
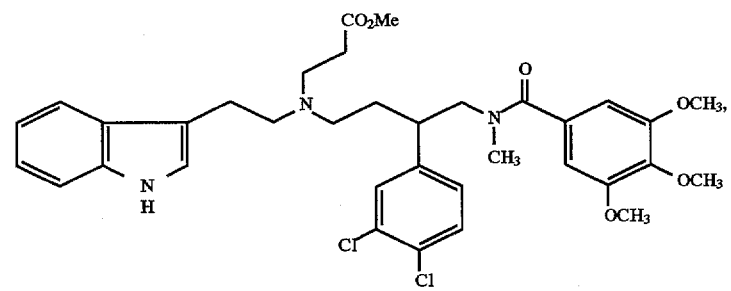

-continued
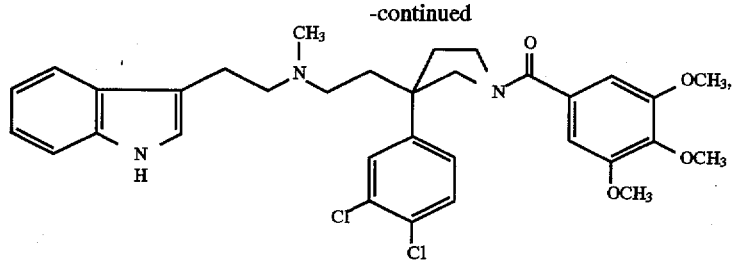
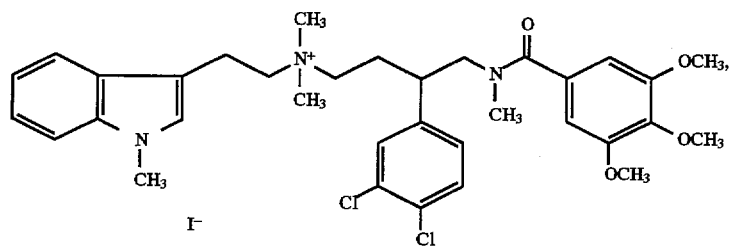
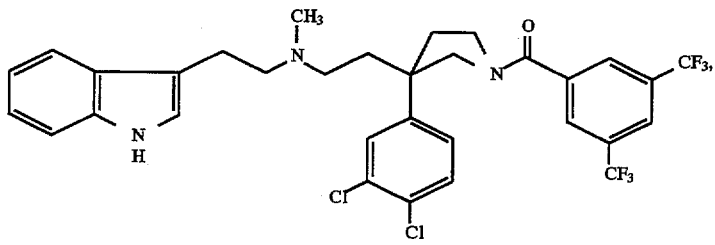
and a compound of the formula
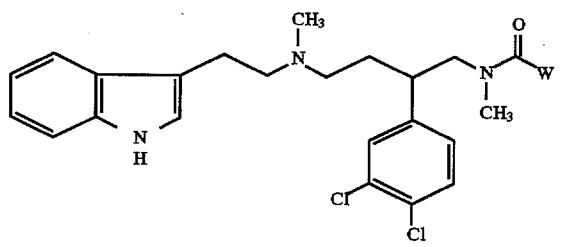
wherein W is
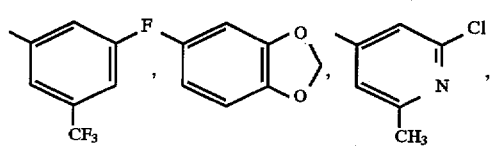
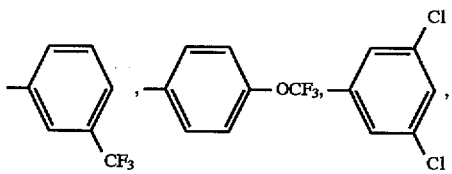
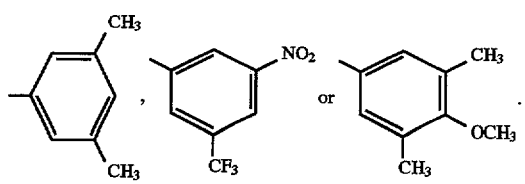
19. A pharmaceutical composition comprising an effective amount of a compound of claim 1 in a pharmaceutically acceptable carrier.

20. A method of treating a disease or condition selected from the group consisting of asthma, cough, bronchospasm, central nervous system diseases, inflammatory diseases and gastrointestinal disorders comprising administering an effective amount of a compound of claim 1 to a mammal in need of such treatment.

* * * * *